US012653936B2

(12) United States Patent
Creech et al.

(10) Patent No.: US 12,653,936 B2
(45) Date of Patent: Jun. 16, 2026

(54) SYSTEM AND METHOD FOR CONTROLLING OXYGEN-ENRICHMENT THERAPY BASED ON MICROVASCULAR RESISTANCE FEEDBACK

(71) Applicant: Zoll Circulation, Inc., San Jose, CA (US)

(72) Inventors: Jeffrey Lance Creech, Los Angeles, CA (US); Stephen Elwood Myrick, Tustin, CA (US); Richard A. Helkowski, Redwood City, CA (US); Fred Shen, San Carlos, CA (US); Ramu Perumal, Gibsonia, PA (US); Gary A. Freeman, Waltham, MA (US)

(73) Assignee: Zoll Circulation, Inc., San Jose, CA (US)

( * ) Notice: Subject to any disclaimer, the term of this patent is extended or adjusted under 35 U.S.C. 154(b) by 466 days.

(21) Appl. No.: 18/182,115

(22) Filed: Mar. 10, 2023

(65) Prior Publication Data

US 2023/0293799 A1 Sep. 21, 2023

Related U.S. Application Data

(60) Provisional application No. 63/319,174, filed on Mar. 11, 2022.

(51) Int. Cl.
*A61M 1/36* (2006.01)
*A61M 1/16* (2006.01)
(Continued)

(52) U.S. Cl.
CPC ........ *A61M 1/3639* (2013.01); *A61M 1/1698* (2013.01); *A61M 1/3607* (2014.02);
(Continued)

(58) Field of Classification Search
CPC ............ A61M 1/1698; A61M 2230/30; A61M 1/3639; A61M 1/3607; A61M 60/38; A61M 60/515; A61M 60/113; A61M 2205/3334
See application file for complete search history.

(56) References Cited

U.S. PATENT DOCUMENTS 6,582,387 B2 6/2003 Derek et al.
6,676,900 B1 1/2004 Divino et al.
(Continued)

FOREIGN PATENT DOCUMENTS

WO WO 2021/202603 10/2021

OTHER PUBLICATIONS

Booth KL, Roth SJ, Perry SB, del Nido PJ, Wessel DL, and Laussen PC. Cardiac catheterization of patients supported by extracorporeal membrane oxygenation. J Amer. Coll. Cardiology, 40:9 (1681-1686) (2002). (Year: 2002).*
(Continued)

*Primary Examiner* — Leslie R Deak
(74) *Attorney, Agent, or Firm* — Fish & Richardson P.C.

(57) ABSTRACT

The present disclosure provides systems and methods for controlling gas-enrichment, e.g., oxygen-enrichment, therapy. One or more sensors and/or one or more imaging systems may be used to measure or determine one or more physiological parameters of the patient. Feedback regarding one or more physiological parameters or microvascular resistance may be provided for titrating or controlling the gas-enrichment therapy.

22 Claims, 10 Drawing Sheets

(51) Int. Cl.

| | | |
|---|---|---|
| *A61M 60/113* | (2021.01) | |
| *A61M 60/38* | (2021.01) | |
| *A61M 60/515* | (2021.01) | |
| *A61M 60/279* | (2021.01) | |

(52) U.S. Cl.

CPC .......... *A61M 60/38* (2021.01); *A61M 60/515* (2021.01); *A61M 60/113* (2021.01); *A61M 60/279* (2021.01); *A61M 2205/18* (2013.01); *A61M 2205/3334* (2013.01); *A61M 2230/04* (2013.01); *A61M 2230/65* (2013.01)

(56) References Cited

U.S. PATENT DOCUMENTS

| | | | |
|---|---|---|---|
| 6,743,196 | B2 | 6/2004 | Barbut et al. |
| 7,820,102 | B2 | 10/2010 | Myrick et al. |
| 8,246,564 | B2 | 8/2012 | Myrick et al. |
| 9,919,276 | B2 | 3/2018 | Myrick et al. |
| 2003/0095892 | A1 | 5/2003 | Patterson et al. |
| 2003/0194348 | A1 | 10/2003 | Divino et al. |
| 2013/0269416 | A1* | 10/2013 | Myrick .................. G01N 29/02 |
| | | | 73/19.03 |
| 2015/0057589 | A1 | 2/2015 | Thomas |
| 2021/0236802 | A1 | 8/2021 | Buckley et al. |
| 2023/0158223 | A1* | 5/2023 | Kapur .............. A61M 25/0662 |
| | | | 604/96.01 |

OTHER PUBLICATIONS

PCT International Search Report and Written Opinion in International Appln. No. PCT/US2023/064128, mailed on Oct. 16, 2023, 17 pages.

PCT International Preliminary Report on Patentability in International Appln. No. PCT/US2023/064128, mailed on Sep. 26, 2024, 12 pages.

Extended European Search Report in European Appln. No. 23767742.2, mailed on Feb. 20, 2026, 7 pages.

\* cited by examiner

100

Sensing / Imaging Device   338

Probe / Catheter   136

Imaging/IMR System   356

500

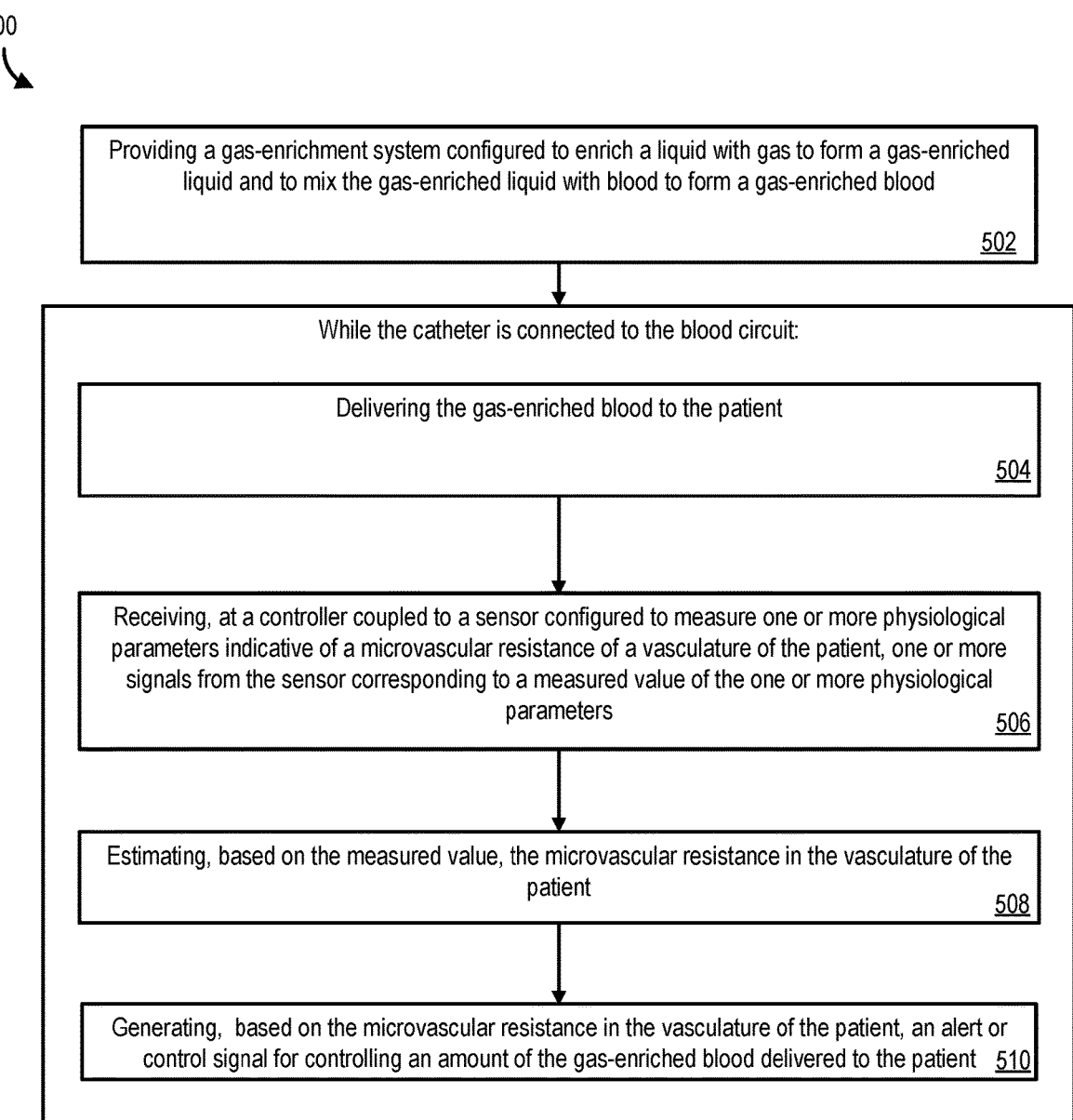

Providing a gas-enrichment system configured to enrich a liquid with gas to form a gas-enriched liquid and to mix the gas-enriched liquid with blood to form a gas-enriched blood

502

While the catheter is connected to the blood circuit:

Delivering the gas-enriched blood to the patient

504

Receiving, at a controller coupled to a sensor configured to measure one or more physiological parameters indicative of a microvascular resistance of a vasculature of the patient, one or more signals from the sensor corresponding to a measured value of the one or more physiological parameters

506

Estimating, based on the measured value, the microvascular resistance in the vasculature of the patient

508

Generating, based on the microvascular resistance in the vasculature of the patient, an alert or control signal for controlling an amount of the gas-enriched blood delivered to the patient   510

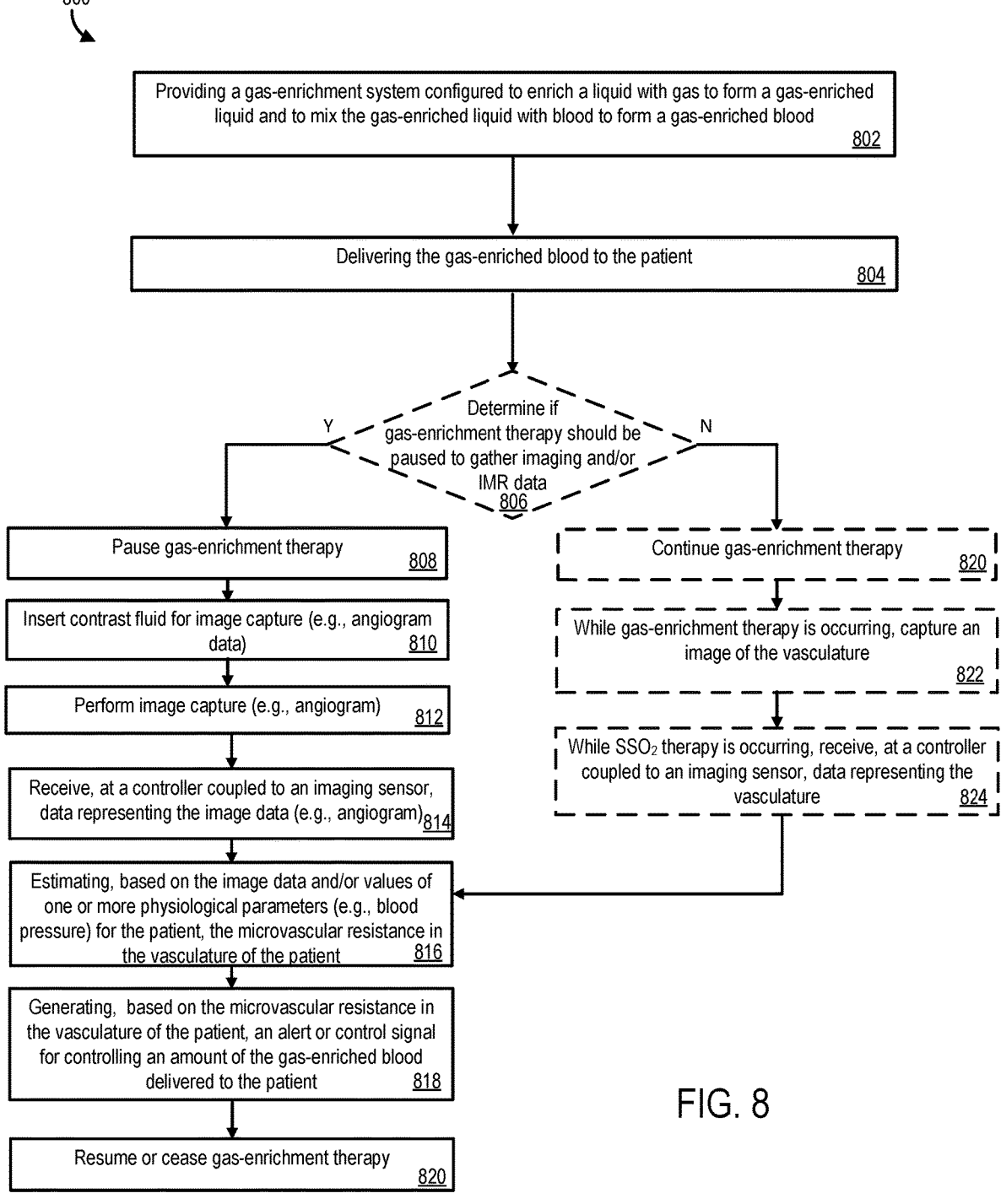

Providing a gas-enrichment system configured to enrich a liquid with gas to form a gas-enriched liquid and to mix the gas-enriched liquid with blood to form a gas-enriched blood
802

Delivering the gas-enriched blood to the patient
804

Determine if gas-enrichment therapy should be paused to gather imaging and/or IMR data
806

Y

N

Pause gas-enrichment therapy     808

Insert contrast fluid for image capture (e.g., angiogram data)     810

Perform image capture (e.g., angiogram)     812

Receive, at a controller coupled to an imaging sensor, data representing the image data (e.g., angiogram)     814

Estimating, based on the image data and/or values of one or more physiological parameters (e.g., blood pressure) for the patient, the microvascular resistance in the vasculature of the patient     816

Generating, based on the microvascular resistance in the vasculature of the patient, an alert or control signal for controlling an amount of the gas-enriched blood delivered to the patient     818

Resume or cease gas-enrichment therapy     820

Continue gas-enrichment therapy     820

While gas-enrichment therapy is occurring, capture an image of the vasculature     822

While $SSO_2$ therapy is occurring, receive, at a controller coupled to an imaging sensor, data representing the vasculature     824

FIG. 8

SYSTEM AND METHOD FOR CONTROLLING OXYGEN-ENRICHMENT THERAPY BASED ON MICROVASCULAR RESISTANCE FEEDBACK

CLAIM OF PRIORITY

This application claims priority under 35 U.S.C. § 119(e) to U.S. patent application Ser. No. 63/319,174, filed on Mar. 11, 2022, the entire contents of which are hereby incorporated by reference.

TECHNICAL FIELD

The disclosure relates to systems and methods for the delivery of gas-enriched liquid or blood into a patient.

BACKGROUND

Gas-enriched liquids are desirable in a wide variety of applications. However, at ambient pressure, the relatively low solubility of many gases, such as oxygen or nitrogen, within a liquid, such as water, produces a relatively low concentration of the dissolved gas in the liquid. One method of obtaining an increase in the gas concentration level without significant increase in liquid volume involves an injection and mixing of a gas-enriched liquid, into a liquid of interest. A liquid can be gas-enriched at high pressure.

Conventional methods for the delivery of oxygenated blood or oxygen-enriched liquids to tissues and bodily liquids involve the use of extracorporeal circuits for blood oxygenation. Extracorporeal circuits require withdrawing blood from a patient, circulating the blood through an oxygenator to increase blood oxygen concentration, and then delivering the blood back to the patient.

SUMMARY

This document describes a gas-enrichment system configured to deliver gas-enriched blood intravenously to a patient. The system for delivering gas-enriched blood within the vasculature of a patient (hereinafter the delivery system) is configured to connect to a catheter device to deliver the gas-enriched blood to the patient. The delivery system includes a blood circuit having a draw line and a return line. The draw line and return line are configured to connect to the catheter. Blood is withdrawn from the patient via the draw line. The blood is mixed with a gas-enriched liquid, or oxygen-enriched liquid such as a supersaturated oxygen (SSO2) enriched liquid, to create gas-enriched blood or supersaturated oxygen-enriched blood. The gas-enriched blood is delivered back to the patient through the catheter by the return line, for example, to provide localized delivery of gas enriched blood to ischemic tissue in the patient. For example, $SSO_2$ therapy may deliver gas-enriched arterial blood directly to at-risk or ischemic myocardial tissue, increasing oxygen diffusion to the ischemic zone, thereby reducing endothelial swelling and microvascular resistance in the microvasculature, and restoring microvascular flow.

The present disclosure provides systems and methods for monitoring, analyzing, delivering and/or controlling gas enrichment therapy or supersaturated oxygen or gas therapy. One or more sensors may be used to measure one or more physiological parameters, e.g., blood or tissue parameters, e.g., pressure and/or flow, of the patient. A processor may be used to estimate, based on the measured parameters, the microvascular resistance in the vasculature of the patient, and generate, based on the microvascular resistance in the vasculature of the patient, an alert or control signal for titrating or controlling the gas-enriched blood delivered to the patient. According to a first example, a system for monitoring, analyzing, delivering and/or controlling gas-enrichment therapy are disclosed. The system includes a gas enrichment system configured to enrich a liquid with gas to form a gas enriched liquid and to mix the gas enriched liquid with blood, e.g., arterial blood, which may form gas enriched blood. The systems may include a plurality of fluid conduits fluidly coupled to the gas enrichment system. At least one conduit of the plurality of fluid conduits is configured for flow of the blood from the patient to the gas enrichment system, and at least one conduit of the plurality of conduits is configured for flow of gas-enriched blood from the gas enrichment system to the patient. The system includes a blood pump coupled to at least one conduit of the plurality of fluid conduits, for pumping blood to and from the gas enrichment system and the patient. The system includes at least one sensor configured to measure one or more physiological parameters. The system may include a user interface configured to receive user input and emit at least one of a visual alert and an audible alert and a controller. The controller includes a processor, a memory, and associated circuitry communicatively coupled to the at least one sensor and the user interface. The controller or processor is configured to receive one or more signals corresponding to a measured value of the one or more physiological parameters from the at least one sensor and estimate, based on the measured parameters, the microvascular resistance in the vasculature of the patient, and generate, based on the microvascular resistance in the vasculature of the patient, an alert or control signal for titrating or controlling the gas-enriched blood delivered to the patient.

In certain implementations, a delivery system for controlling gas-enrichment therapy in a patient includes a gas-enrichment system configured to enrich a liquid with gas to form a gas-enriched liquid and to deliver the gas-enriched liquid into a vasculature of the patient, where a gas-enriched blood if formed in the vasculature of the patient. At least one conduit is fluidly coupled to the gas-enrichment system, and the at least one conduit configured for flow of the gas-enriched liquid from the gas-enrichment system to the patient. a pump coupled to the at least one conduit, the pump configured to pump gas-enriched liquid from the gas-enrichment system to the patient. The system includes at least one sensor configured to measure one or more physiological parameters indicative of a microvascular resistance in a vasculature of the patient. The system includes a processor, a memory, and associated circuitry communicatively coupled to the at least one sensor. The processor is configured to receive one or more signals corresponding to a measured value of the one or more physiological parameters from the at least one sensor; estimate, based on the measured value, the microvascular resistance in the vasculature of the patient; and generate, based on the microvascular resistance in the vasculature of the patient, an alert or control signal for titrating or controlling the gas-enriched liquid delivered to the patient.

The systems and methods described herein provide one or more advantages. The delivery system enables a closed-loop feedback system for applying gas-enrichment therapy, e.g., $SSO_2$ therapy to a patient. The delivery system enables real-time or near-real time measurements of regional myocardial blood flow and/or estimates of microvascular resistance in the patient. The measurements and/or estimates allow the delivery system to determine the patient's response to gas-enrichment therapy and modify, e.g., stop or change, the therapy during treatment without pausing the treatment. For example, the delivery system can estimate if the gas-enrichment therapy is reducing microvascular resistance or improving microvascular flow, e.g., regionally or locally in the vascular of the patient, e.g., in the microvasculature of the Left Main Coronary (LMC), in real time or near real time, and providing real time or near real time feedback to optimize gas-enrichment therapy.

The feedback enables the user to determine with precision when to end gas-enrichment delivery or whether to continue gas-enrichment therapy. The delivery system provides data to a user (e.g., a physician) to enable the user to determine how long to deliver gas-enrichment therapy and determine whether gas-enrichment therapy is succeeding. In some implementations, the feedback enables the delivery system to provide automated alerts or trigger one or more automated actions to transmit data to a remote device, display information to the user, or change the gas-enrichment treatment. For example, alerts can be sent to a user device or displayed on a user interface. In some implementations, a treatment log may be generated that shows how gas-enrichment therapy affects the patient.

The precise, customized control over the duration, amount or concentration of gas-enrichment therapy provides an increased efficiency for caring for patients and reduces overhead waste of time or other resources. For example, if a microvascular resistance-based gas-enrichment therapy can determine when or to what extent microvascular flow is restored, then gas-enrichment therapy could be reduced (e.g., to a time of less than 60 minutes) or continued for certain patients, depending on the microvascular resistance (e.g., IMR value) of the patient. This can improve patient comfort and reduce use of caregiver resources. In some implementations, the quality of the gas-enrichment therapy is improved, even if an overall duration is comparable to treatment without feedback. In some implementations, the delivery system enables non-invasive confirmation of whether gas-enrichment therapy is effective.

In certain implementations, an index of microcirculatory resistance (IMR) can be deduced or estimated, and control of the gas-enrichment therapy can be adjusted based on the IMR values. IMR is a quantitative, reproducible index which is independent of epicardial coronary disease and specific for the microcirculation and which can be measured relatively easily at the time of ST Elevation Myocardial Infarction (STEMI). A heart attack with a completely blocked coronary artery is called a STEMI. In some implementations, IMR includes a pressure-temperature sensor guidewire-based measurement, performed during cardiac catheterization, of the minimum microcirculatory resistance in a target coronary artery territory. In some implementations, IMR may be deduced from imaging data, such as an angiogram or magnetic resonance image (MRI).

One or more of the advantages described herein can be enabled by one or more of the following embodiments.

In a general aspect, a system for controlling gas-enrichment therapy in a patient is provided. The system including a gas-enrichment system configured to enrich a liquid with gas to form a gas-enriched liquid and to mix the gas-enriched liquid with blood to form gas-enriched blood. The system includes a plurality of fluid conduits fluidly coupled to the gas-enrichment system, a first conduit of the plurality of fluid conduits configured for flow of the blood from the patient to the gas-enrichment system. The system includes a second conduit of the plurality of conduits that is configured for flow of the gas-enriched blood from the gas-enrichment system to the patient. The system includes a pump coupled to at least one conduit, of the plurality of fluid conduits. The pump is configured to pump blood to and from the gas-enrichment system and the patient. The system includes at least one sensor configured to measure one or more physiological parameters indicative of a microvascular resistance in a vasculature of the patient. The system includes a controller comprising a processor, a memory, and associated circuitry communicatively coupled to the at least one sensor. The processor is configured to perform operations including: receiving one or more signals corresponding to a measured value of the one or more physiological parameters from the at least one sensor; estimating, based on the measured value, a microvascular resistance in the vasculature of the patient; and generating, based on the estimated microvascular resistance in the vasculature of the patient, an alert or control signal for controlling an amount of the gas-enriched blood delivered to the patient.

In some implementations, the operations may include determining a change in the microvascular resistance of the vasculature of the patient. The operations may include generating based on the determined change in microvascular resistance, an alert or control signal for controlling an amount of the gas-enriched blood delivered to the patient.

In some implementations, the at least one sensor comprises a flow sensor. The one or more physiological parameters may comprise a flow rate of blood in the vasculature of the patient.

In some implementations, the at least one sensor may comprise a pressure sensor. The one or more physiological parameters may comprise a pressure of blood in the vasculature of the patient.

In some implementations, the operations may include sending the control signal to the pump during operation of the pump for delivery of the gas-enriched blood to the patient. The operations may include causing, based on sending the control signal, the pump to increase a pump speed or reduce a pump speed to increase or reduce the amount of the gas-enriched blood delivered to the patient.

In some implementations, controlling the amount of the gas-enriched blood delivered to the patient may include determining that a change in the value of the one or more physiological parameters represents a reduced microvascular resistance in the vasculature of the patient. Controlling the amount of the gas-enriched blood delivered to the patient may include, in response to determining that the change in the value represents the reduced microvascular resistance, generating the control signal that is configured to cause a reduction in the amount of the gas-enriched blood delivered to the patient.

In some implementations, controlling the amount of the gas-enriched blood delivered to the patient may include determining that a change in the value of the one or more physiological parameters represents an increased microvascular resistance in the vasculature of the patient. Controlling the amount of the gas-enriched blood delivered to the patient may include in response to determining that the change in the value represents the increased microvascular resistance, generating the control signal that is configured to cause an increase in the amount of the gas-enriched blood delivered to the patient.

In some implementations, the at least one sensor may comprise a flow sensor and a pressure sensor. The physiological parameters may comprise a flow rate of the blood in the vasculature of the patient and a blood pressure in the vasculature of the patient. The operations may further include estimating a change in microvascular resistance in the patient based on a ratio of the blood pressure and the flow rate. The operations may include generating the control signal based on the estimated microvascular resistance.

In some implementations, generating the control signal may be performed in real-time or near-real time during delivery of the gas-enriched blood to the patient. The delivery of the gas-enriched blood to the patient may not be paused during measurement of the one or more physiological parameters. The measurement of the one or more physiological parameters may represent a contemporaneous status of the patient for the delivery of the gas-enriched blood to the patient.

In some implementations, real-time or near-real time may comprise processing, by the controller, data received from the one or more sensors as soon as the data are available to the controller and generating the control signal based on the processing.

In some implementations, receiving one or more signals corresponding to a measured value of the one or more physiological parameters from the at least one sensor may comprise receiving a series of measured values of the one or more physiological parameters from the at least one sensor. The series of measured values may correspond to a period of time during delivery of the gas-enriched blood to the patient. The operations may further include determining, optionally based on the series of measured values corresponding to the period of time, whether the value of the one or more physiological parameters is increasing or decreasing over time. The operations may include generating, optionally based on determining that the value of the one or more physiological parameters increasing or decreasing over time, the control signal configured to increase or reduce the amount of the gas-enriched blood delivered to the patient.

In some implementations, the operations further may include receiving angiogram data representing the patient for a time period contemporaneous with delivery of the gas-enriched blood to the patient. The operations may include determining an IMR from the angiogram data. The operations may include generating, based on the angiogram data and determined IMR or change in IMR, the control signal configured to increase or reduce the amount of the gas-enriched blood delivered to the patient.

In some implementations, the system may include a catheter configured to deliver the gas-enriched blood to the patient. The system may include and a wire coupled to the catheter. The wire may comprise the at least one sensor. Said at least one sensor may be a pressure sensor. The pressure sensor may be configured to obtain pressure data in the vasculature of the patient. The operations may further include receiving the pressure data from the pressure sensor. The operations may include determining, based on the pressure data, an Index of Microcirculatory Resistance (IMR) value in the vasculature of the patient. The operations may include generating, optionally based on the IMR value or a change in IMR value, the control signal configured to increase or reduce the amount of the gas-enriched blood delivered to the patient.

In some implementations, the system may include at least one sensor comprising a plurality of sensors. The plurality of sensors may comprise a plurality of electrodes, which may be configured for placement on an exterior of the patient. The operations may include measuring impedance values from a tissue area between one or more pairs of the plurality of electrodes. The operations may include generating an impedance tomographic map based at least in part on the measured impedance values. The operations may include, optionally based at least in part on an impedance distribution of the impedance tomographic map, estimating the microvascular resistance of a region of vasculature of the patient.

In some implementations, the region of vasculature is a cardiac region.

In some implementations, the region of vasculature is a region of muscle.

In some implementations, estimating is based at least in part on an average impedance of the impedance distribution.

In some implementations, estimating is based at least in part on a product of local impedance and volume of the impedance distribution.

In some implementations, the gas-enrichment system is configured to enrich a liquid with oxygen to form an oxygen-enriched liquid to be mixed with blood.

In some implementations, the gas-enrichment system comprises a cartridge.

In some implementations, the cartridge has three chambers.

In some implementations, the physiological parameter comprises an electrical activity, of a heart of the patient, measured by an electrocardiogram (ECG) sensor.

In some implementations, estimating comprises estimating a microvascular resistance in a localized or regional area of the vasculature of the patient.

In some implementations, controlling comprises titrating the amount of the gas-enriched blood delivered to the patient.

In a general aspect, a system for controlling gas-enrichment therapy in a patient is provided. The system includes a gas-enrichment system configured to enrich a liquid with gas to form a gas-enriched liquid and to mix the gas-enriched liquid with arterial blood to form gas-enriched blood; a plurality of fluid conduits fluidly coupled to the gas-enrichment system, a first conduit of the plurality of fluid conduits configured for flow of the blood from the patient to the gas-enrichment system, and a second conduit of the plurality of conduits configured for flow of the gas-enriched blood from the gas-enrichment system to the patient; a pump coupled to at least one conduit of the plurality of fluid conduits, the pump configured to pump blood to and from the gas-enrichment system and the patient; a catheter coupled to one or more of the plurality of fluid conduits and configured to deliver the gas-enriched blood from the gas-enrichment system to the patient based on operation of the pump; a wire coupled to the catheter or a separate probe, the wire configured to extend along the catheter or probe to a distal tip of the catheter or probe; a pressure sensor coupled to the wire at the distal tip of the catheter or probe, the pressure sensor configured to measure a blood pressure in a vasculature the patient; and a controller comprising a processor, a memory, and associated circuitry communicatively coupled to the pressure sensor, wherein the processor is configured to perform operations. The operations include determining, based on the measured blood pressure, a change in blood pressure in the vasculature of the patient; determining blood flow in the vasculature of the patient; estimating, based on a ratio of the blood pressure change and blood flow in the vasculature of the patient, a microvascular resistance in the vasculature of the patient; and generating, based on the microvascular resistance in the vasculature of the patient, an alert or control signal for controlling an amount of the gas-enriched blood delivered to the patient.

In some implementations, estimating comprises estimating a microvascular resistance in a localized or regional area of the vasculature of the patient.

In some implementations, the controlling comprises titrating the amount of the gas-enriched blood delivered to the patient.

In a general aspect, a process for controlling gas-enrichment therapy in a patient is provided. The process includes providing a gas-enrichment system configured to enrich a liquid with gas to form a gas-enriched liquid and to mix the gas-enriched liquid with blood to form a gas-enriched blood; delivering the gas-enriched blood to the patient; receiving, at a controller coupled to a sensor configured to measure one or more physiological parameters indicative of a microvascular resistance of a vasculature of the patient, one or more signals from the sensor corresponding to a measured value of the one or more physiological parameters; estimating, based on the measured value, the microvascular resistance in the vasculature of the patient; and generating, based on the microvascular resistance in the vasculature of the patient, an alert or control signal for controlling an amount of the gas-enriched blood delivered to the patient.

In some implementations, the control signal may be configured to control a pump configured to pump the gas-enriched blood for delivery into the patient. The process may include causing the pump to pump blood to and from the gas-enrichment system and the patient based on sending the control signal to the pump.

In some implementations, the sensor may comprise a flow sensor. The one or more physiological parameters may comprise a flow rate of blood in the vasculature of the patient.

In some implementations, the sensor may comprise a pressure sensor. The one or more physiological parameters may comprise a pressure of blood in the vasculature of the patient.

In some implementations, the process may include sending, by the controller, the control signal to a pump configured to pump the gas-enriched blood for delivery into the patient. The process may include causing, optionally based on sending the control signal, the pump to increase a pump speed or reduce a pump speed to increase or reduce the amount of the gas-enriched blood delivered to the patient.

In some implementations, reducing the amount of the gas-enriched blood delivered to the patient may include: determining that a change in the value of the one or more physiological parameters represents a reduced microvascular resistance in the vasculature of the patient. Reducing the amount of gas-enriched blood delivered to the patient may include, optionally in response to determining that the change in the value represents the reduced microvascular resistance, generating the control signal that is configured to cause a reduction in the amount of the gas-enriched blood delivered to the patient.

In some implementations, increasing the amount of the gas-enriched blood delivered to the patient may include determining that a change in the value of the one or more physiological parameters represents an increased microvascular resistance in the vasculature of the patient. Increasing the amount of gas-enriched blood delivered to the patient may include in response to determining that the change in the value represents the increased microvascular resistance, generating the control signal that is configured to cause an increase in the amount of the gas-enriched blood delivered to the patient.

In some implementations, the sensor may comprise a flow sensor and a pressure sensor, wherein the physiological parameters comprise a flow rate of the blood in the vasculature of the patient and a blood pressure in the vasculature of the patient. The process may include estimating a microvascular resistance in the patient based on a ratio of the flow rate and the blood pressure. The process may include generating the control signal based on the estimated microvascular resistance.

In some implementations, generating the control signal may be performed in real-time or near-real time during delivery of the gas-enriched blood to the patient. The delivery of the gas-enriched blood to the patient may not be paused during measurement of the one or more physiological parameters. The measurement of the one or more physiological parameters may represent a contemporaneous status of the patient for the delivery of the gas-enriched blood to the patient.

In some implementations, receiving one or more signals corresponding to a measured value of the one or more physiological parameters from the sensor may comprise receiving a series of measured values of the one or more physiological parameters from the sensor. The series of measured values may correspond to a period of time during delivery of the gas-enriched blood to the patient. The process may include determining, optionally based on the series of measured values corresponding to the period of time, whether the value of the one or more physiological parameters is increasing or decreasing over time. The process may include generating, optionally based on determining that the value of the one or more physiological parameters increasing or decreasing over time, the control signal configured to increase or reduce the amount of the gas-enriched blood delivered to the patient.

In some implementations, the process may include receiving angiogram data representing the patient for a time period contemporaneous with delivery of the gas-enriched blood to the patient. The process may include determining an IMR from the angiogram data. The process may include generating, optionally based on the angiogram data and determined IMR or change in IMR, the control signal configured to increase or reduce the amount of the gas-enriched blood delivered to the patient.

In some implementations, the process may include receiving, optionally by the controller, pressure data from a pressure sensor coupled to a wire supported at a distal end of a catheter in the vasculature of the patient. The process may include determining, by the controller based on the pressure data, an Index of Microcirculatory Resistance (IMR) value in the vasculature of the patient. The process may include generating, optionally by the controller based on the IMR value or a change in IMR value, the control signal configured to increase or reduce the amount of the gas-enriched blood delivered to the patient.

In some implementations, the process may include measuring, optionally by the controller, impedance values from a tissue area between one or more pairs of a plurality of external electrodes configured for placement on an exterior of the patient. The process may include generating, optionally by the controller, an impedance tomographic map based at least in part on the measured impedance values. The process may include, optionally based at least in part on an impedance distribution of the impedance tomographic map, estimating the microvascular resistance of a region of vasculature of the patient In some implementations, the region of vasculature is a cardiac region.

In some implementations, the region of vasculature is a region of muscle.

In some implementations, the estimating is based at least in part on an average impedance of the impedance distribution.

In some implementations, the estimating is based at least in part on a product of local impedance and volume of the impedance distribution.

In some implementations, the controlling comprises titrating the amount of the gas-enriched blood delivered to the patient.

In a general aspect, a system for controlling gas-enrichment therapy in a patient is provided. The system includes a gas-enrichment system configured to enrich a liquid with gas to form a gas-enriched liquid and to deliver the gas-enriched liquid into a vasculature of the patient to form gas-enriched blood; at least one conduit fluidly coupled to the gas-enrichment system, the at least one conduit configured for flow of the gas-enriched liquid from the gas-enrichment system to the patient; a pump coupled to the at least one conduit, the pump configured to pump gas-enriched liquid from the gas-enrichment system to the patient; at least one sensor configured to measure one or more physiological parameters indicative of a microvascular resistance in a vasculature of the patient; and a controller comprising a processor, a memory, and associated circuitry communicatively coupled to the at least one sensor. The processor is configured to perform operations. The operations include receiving one or more signals corresponding to a measured value of the one or more physiological parameters from the at least one sensor; estimating, based on the measured value, the microvascular resistance in the vasculature of the patient; and generating, based on the microvascular resistance in the vasculature of the patient, an alert or control signal for titrating or controlling the gas-enriched liquid delivered to the patient.

In some implementations, the operations may include determining a change in the microvascular resistance of the vasculature of the patient. The operations may include generating based on the determined change in microvascular resistance, an alert or control signal for titrating or controlling the gas-enriched liquid delivered to the patient.

In some implementations, the at least one sensor may comprise a flow sensor. The one or more physiological parameters may comprise a flow rate of blood in the vasculature of the patient.

In some implementations, the at least one sensor may comprise a pressure sensor. The one or more physiological parameters may comprise a pressure of blood in the vasculature of the patient.

In some implementations, operations may include sending the control signal to the pump during operation of the pump for delivery of the gas-enriched liquid to the patient. The operations may include causing, based on sending the control signal, the pump to increase a pump speed or reduce a pump speed to increase or reduce the amount of the gas-enriched liquid delivered to the patient.

In some implementations, controlling the amount of the gas-enriched blood delivered to the patient may comprise: determining that a change in the value of the one or more physiological parameters represents a reduced microvascular resistance in the vasculature of the patient. Controlling the amount of the gas-enriched blood delivered to the patient may comprise in response to determining that the change in the value represents the reduced microvascular resistance, generating the control signal that is configured to cause a reduction in the amount of the gas-enriched liquid delivered to the patient.

In some implementations, controlling the amount of the gas-enriched liquid delivered to the patient may comprise determining that a change in the value of the one or more physiological parameters represents an increased microvascular resistance in the vasculature of the patient. Controlling the amount of the gas-enriched blood delivered to the patient may include, optionally in response to determining that the change in the value represents the increased microvascular resistance, generating the control signal that is configured to cause an increase in the amount of the gas-enriched liquid delivered to the patient.

In some implementations, the at least one sensor may comprise a flow sensor and a pressure sensor. The physiological parameters may comprise a flow rate of the blood in the vasculature of the patient and a blood pressure in the vasculature of the patient. The operations may include estimating a change in microvascular resistance in the patient based on a ratio of the blood pressure and the flow rate. The operations may include generating the control signal or alert based on the estimated microvascular resistance.

In some implementations, generating the control signal or alert may be performed in real-time or near-real time during delivery of the gas-enriched liquid to the patient. The delivery of the gas-enriched liquid to the patient may not be paused during measurement of the one or more physiological parameters. The measurement of the one or more physiological parameters may represent a contemporaneous status of the patient for the delivery of the gas-enriched liquid to the patient.

In some implementations, real-time or near-real time may comprise processing, optionally by the controller, data received from the one or more sensors as soon as the data are available to the controller and generating the control signal or alert based on the processing.

In some implementations, receiving one or more signals corresponding to a measured value of the one or more physiological parameters from the at least one sensor may comprise receiving a series of measured values of the one or more physiological parameters from the at least one sensor. The series of measured values may correspond to a period of time during delivery of the gas-enriched liquid to the patient. The operations may include determining, optionally based on the series of measured values corresponding to the period of time, whether the value of the one or more physiological parameters is increasing or decreasing over time. The operations may include generating, based on determining that the value of the one or more physiological parameters is increasing or decreasing over time, the control signal or alert to increase or reduce the amount of the gas-enriched liquid delivered to the patient.

In some implementations, the operations may include receiving angiogram data representing the patient for a time period contemporaneous with delivery of the gas-enriched liquid to the patient. The operations may include determining an IMR from the angiogram data. The operations may include generating, optionally based on the angiogram data and determined IMR or change in IMR, the control signal or alert to increase or reduce the amount of the gas-enriched liquid delivered to the patient.

In some implementations, the at least one sensor may comprise a plurality of sensors. The plurality of sensors may comprise a plurality of electrodes configured for placement on an exterior of the patient. The operations may include measuring impedance values from a tissue area between one or more pairs of the plurality of electrodes. The operations may include generating an impedance tomographic map based at least in part on the measured impedance values. The operations may include, optionally based at least in part on an impedance distribution of the impedance tomographic map, estimating the microvascular resistance of a region of vasculature of the patient.

In some implementations, the region of vasculature is a cardiac region.

In some implementations, the region of vasculature is a region of muscle.

In some implementations, the estimating is based at least in part on an average impedance of the impedance distribution.

In some implementations, the estimating is based at least in part on a product of local impedance and volume of the impedance distribution.

In some implementations, the gas-enrichment system is configured to enrich a liquid with oxygen to form an oxygen-enriched liquid to be mixed with blood.

In some implementations, the gas-enrichment system comprises a cartridge.

In some implementations, the cartridge has three chambers.

In some implementations, the controlling comprises titrating the amount of the gas-enriched blood delivered to the patient.

In a general aspect, a system for controlling a gas-enrichment therapy is provided. The system may comprise a gas-enrichment system configured to enrich a liquid with gas to form a gas-enriched liquid and optionally to mix the gas-enriched liquid with blood to form gas-enriched blood. The system may comprise, at least one conduit fluidly coupled to the gas-enrichment system. The at least one conduit may comprise a conduit configurable for flow of the gas-enriched blood or gas-enriched liquid from the gas-enrichment system to the patient. The at least one conduit may comprise a conduit configured for flow of the blood from the patient to the gas-enrichment system. The system may comprise a pump coupled to the at least one conduit of the plurality of fluid conduits. The pump may be configurable to pump blood to the gas-enrichment system from the patient. The pump may be configurable to pump blood from the gas-enrichment system to the patient. The pump may be configurable to pump gas-enriched liquid or gas-enriched blood from the gas-enrichment system to the patient. The system may comprise at least one sensor configurable to measure one or more physiological parameters indicative of a microvascular resistance in a vasculature of the patient. The system may comprise a controller configurable to perform operations comprising one or more of: receiving one or more signals corresponding to a measured value of the one or more physiological parameters from the at least one sensor; estimating, based on the measured value, the microvascular resistance in the vasculature of the patient; and generating, based on the microvascular resistance in the vasculature of the patient, an alert or control signal for titrating or controlling the gas-enriched blood or gas-enriched liquid delivered to the patient.

In a general aspect there is provided a system comprising: a gas-enrichment system configured to enrich a liquid with gas to form a gas-enriched liquid; a pump configured to pump a fluid from the gas-enrichment system to the patient, wherein the fluid comprises the gas-enriched liquid; at least one sensor configured to measure one or more physiological parameters indicative of a microvascular resistance in a vasculature of the patient; and a controller configured to perform operations comprising: receiving one or more signals corresponding to a measured value of the one or more physiological parameters from the at least one sensor; estimating, based on the measured value, a microvascular resistance in the vasculature of the patient; and generating, based on the estimated microvascular resistance in the vasculature of the patient, an alert or control signal for titrating or controlling the fluid delivered to the patient. The gas-enrichment system may be configured to mix the gas-enriched liquid with blood to form the gas-enriched blood. The fluid may be the gas-enriched liquid or gas-enriched blood.

In a general aspect, a system for controlling gas-enrichment therapy in a patient, is provided. The system includes a gas-enrichment system configured to enrich a liquid with gas to form a gas-enriched liquid and to deliver the gas-enriched liquid into a vasculature of the patient to form gas-enriched blood; at least one conduit fluidly coupled to the gas-enrichment system, the at least one conduit configured for flow of the gas-enriched liquid from the gas-enrichment system to the patient; a pump coupled to the at least one conduit, the pump configured to pump gas-enriched liquid from the gas-enrichment system to the patient; at least one sensor configured to measure one or more physiological parameters in a vasculature of the patient; at least one sensor configured to measure one or more physiological parameters in a vasculature of the patient; and one or more controllers comprising a processor, a memory, wherein the one or more controllers are configured to perform operations. The operations include receiving one or more signals corresponding to a measured value of the one or more physiological parameters from the at least one sensor;

receiving imaging data representing the vasculature of the patient; estimating, based on the imaging data and the one or more signals corresponding to a measured value of the one or more physiological parameters, the microvascular resistance in the vasculature of the patient; and generating, based on the microvascular resistance in the vasculature of the patient, an alert or control signal for titrating or controlling the gas-enriched liquid delivered to the patient.

In some implementations, estimating the microvasculature resistance comprises determining an IMR value. In some implementations, the imaging data is one or more angiogram images. In some implementations, the sensor is a pressure sensor.

In some implementations, the operations further include receiving the imaging data in the form of angiogram data representing the patient, the angiogram data being generated after a delivery of the gas-enriched blood to the patient; determining an IMR from the angiogram data; and generating, based on the angiogram data and determined IMR or change in IMR, an alert or control signal configured to increase or reduce the amount of the gas-enriched blood delivered to the patient.

In some implementations, the at least one sensor is communicatively coupled to the controller and configured to measure one or more physiological parameters indicative of a microvascular resistance in a vasculature of the patient In some implementations, the at least one sensor is configured to transmit one or more signals corresponding to a measured value of the one or more physiological parameters. In some implementations, the at least one or more signals corresponding to a measured value of the one or more physiological parameters corresponds to a pressure or flow value.

In some implementations, the control signal increases or reduces the amount of the gas-enriched blood delivered to the patient without pausing delivery of the gas-enriched blood to the patient.

In a general aspect, a system for controlling oxygen-enrichment therapy in a patient is provided. The system includes an oxygen-enrichment system configured to enrich a liquid with gas to form a gas-enriched liquid and to mix the oxygen-enriched liquid with blood to form oxygen-enriched blood; a plurality of fluid conduits fluidly coupled to the oxygen enrichment system, a first conduit of the plurality of fluid conduits configured for flow of the blood from the patient to the oxygen enrichment system, and a second conduit of the plurality of conduits configured for flow of the oxygen-enriched blood from the oxygen enrichment system to the patient; a pump coupled to at least one conduit of the plurality of fluid conduits, the pump configured to pump blood to and from the oxygen enrichment system and the patient; and one or more controllers comprising a processor, a memory, and associated circuitry, wherein the one or more controllers are configured to perform operations. The operations include delivering oxygen-enriched blood to the patient; after a predetermined period of time, pausing delivery of the oxygen-enriched blood to the patient; capturing one or more angiogram images representing a vasculature of the patient; estimating, based on the one or more angiogram images, an index of microvascular resistance in the vasculature of the patient; generating, based on the estimated index of microvascular resistance in the vasculature of the patient, an alert or an instruction to control delivery of the gas-enriched blood to the patient; and controlling, based on the alert or instruction, the delivery of gas-enriched blood to the patient.

In some implementations, system includes at least one sensor configured to measure pressure or flow in a vasculature of the patient, wherein the one or more controllers are configured to receive one or more signals corresponding to a measured value of the pressure or flow from the at least one sensor, and estimate, based on the imaging data and the one or more signals corresponding to a measured value of pressure or flow, the microvascular resistance in the vasculature of the patient.

In some implementations, the gas-enrichment system is configured to form oxygen-enriched blood. In some implementations, the gas-enrichment system is configured to form oxygen-enriched liquid.

In a general aspect, a system for controlling gas-enrichment therapy in a patient, the system is provided. The system includes a gas-enrichment system configured to enrich a liquid with gas to form a gas-enriched liquid and to mix the gas-enriched liquid with blood to form gas-enriched blood; a plurality of fluid conduits fluidly coupled to the gas-enrichment system, a first conduit of the plurality of fluid conduits configured for flow of the blood from the patient to the gas-enrichment system, and a second conduit of the plurality of conduits configured for flow of the gas-enriched blood from the gas-enrichment system to the patient; a pump coupled to at least one conduit of the plurality of fluid conduits, the pump configured to pump blood to and from the gas-enrichment system and the patient; at least one sensor configured to measure one or more physiological parameters indicative of a microvascular dysfunction in a vasculature of the patient; and one or more controllers comprising a processor, a memory, and associated circuitry, wherein the processor is configured to perform operations. The operations include receiving one or more signals corresponding to a measured value of the one or more physiological parameters from the at least one sensor; estimating, based on the measured value, a microvascular dysfunction in the vasculature of the patient; and generating, based on the estimated microvascular dysfunction in the vasculature of the patient, an alert or control signal for controlling an amount of the gas-enriched blood delivered to the patient.

In some implementations, the one or more signals correspond to a measured value of blood pressure from at least one pressure sensor, a microvascular dysfunction in the vasculature of the patient is estimated based on the measured pressure value and an alert or control signal is generated based on the estimated microvascular dysfunction.

In some implementations, the one or more signals correspond to a measured value of blood flow from at least one flow sensor, a microvascular dysfunction in the vasculature of the patient is estimated based on the measured flow value and an alert or control signal is generated based on the estimated microvascular dysfunction.

In some implementations, the microvascular dysfunction is microvascular obstruction.

In some implementations, the microvascular dysfunction is microvascular resistance.

In a general aspect, a system for controlling gas-enrichment therapy in a patient, the system includes a gas-enrichment system configured to enrich a liquid with gas to form a gas-enriched liquid and to deliver the gas-enriched liquid into a vasculature of the patient to form gas-enriched blood; at least one conduit fluidly coupled to the gas-enrichment system, the at least one conduit configured for flow of the gas-enriched liquid from the gas-enrichment system to the patient; a pump coupled to the at least one conduit, the pump configured to pump gas-enriched liquid from the gas-enrichment system to the patient; at least one sensor configured to measure one or more physiological parameters indicative of a microvascular dysfunction in a vasculature of the patient; and one or more controllers comprising a processor, a memory, and associated circuitry, wherein the processor is configured to perform operations. The operations include receiving one or more signals corresponding to a measured value of the one or more physiological parameters from the at least one sensor; estimating, based on the measured value, the microvascular dysfunction in the vasculature of the patient; and generating, based on the microvascular dysfunction in the vasculature of the patient, an alert or control signal for titrating or controlling the gas-enriched liquid delivered to the patient.

In some implementations, the one or more signals correspond to a measured value of blood pressure from at least one pressure sensor, a microvascular dysfunction in the vasculature of the patient is estimated based on the measured pressure value and an alert or control signal is generated based on the estimated microvascular dysfunction.

In some implementations, the one or more signals correspond to a measured value of blood flow from at least one flow sensor, a microvascular dysfunction in the vasculature of the patient is estimated based on the measured flow value and an alert or control signal is generated based on the estimated microvascular dysfunction.

In some implementations, the microvascular dysfunction is microvascular obstruction.

In some implementations, the microvascular dysfunction is microvascular resistance.

In a general aspect, a system for controlling gas-enrichment therapy in a patient, the system is provided. The system includes a gas-enrichment system configured to enrich a liquid with gas to form a gas-enriched liquid and to mix the gas-enriched liquid with blood to form gas-enriched blood; a plurality of fluid conduits fluidly coupled to the gas-enrichment system, a first conduit of the plurality of fluid conduits configured for flow of the blood from the patient to the gas-enrichment system, and a second conduit of the plurality of conduits configured for flow of the gas-enriched blood from the gas-enrichment system to the patient; a pump coupled to at least one conduit of the plurality of fluid conduits, the pump configured to pump blood to and from the gas-enrichment system and the patient; at least one sensor configured to measure a blood flow for a vasculature of the patient; and one or more controllers comprising a processor, a memory, and associated circuitry, wherein the processor is configured to perform operations. The operations include receiving one or more signals corresponding to a measured value of the blood flow from the at least one sensor; and generating, based on the e measured value of the blood flow, an alert or control signal for controlling an amount of the gas-enriched blood delivered to the patient.

In a general aspect, a system for controlling gas-enrichment therapy in a patient, the system comprising: a gas-enrichment system configured to enrich a liquid with gas to form a gas-enriched liquid and to deliver the gas-enriched liquid into a vasculature of the patient to form gas-enriched blood; at least one conduit fluidly coupled to the gas-enrichment system, the at least one conduit configured for flow of the gas-enriched liquid from the gas-enrichment system to the patient; a pump coupled to the at least one conduit, the pump configured to pump gas-enriched liquid from the gas-enrichment system to the patient; at least one sensor configured to measure a blood flow in a vasculature of the patient; and one or more controllers comprising a processor, a memory, and associated circuitry, wherein the processor is configured to perform operations. The operations include receiving one or more signals corresponding to a measured value of the blood flow from the at least one sensor; generating, based on the blood flow measurement, an alert or control signal for titrating or controlling the gas-enriched liquid delivered to the patient.

In a general aspect, there is provided a computer program. The computer program may be stored in a memory or on a non-transitory processor-readable medium. The computer program is configured to cause at least one processor to perform one or more of the operations described with reference to any preceding aspect.

In a general aspect, the operations performed by a system described herein can be performed as a process by a system, device, or a plurality of devices.

In general, an implementation described with respect to one aspect may be provided in combination with another aspect. The details of one or more embodiments are set forth in the accompanying drawings and the description. Other features and advantages will be apparent from the description and drawings, and from the claims.

BRIEF DESCRIPTION OF THE DRAWINGS

FIG. 5 shows a flow diagram of an example process for controlling delivery of oxygen-enriched blood to a patient based on measurements from physiological parameter sensors.

FIG. 8 is a flow diagram of an example process for controlling delivery of oxygen-enriched blood to a patient.

Figure 1A:
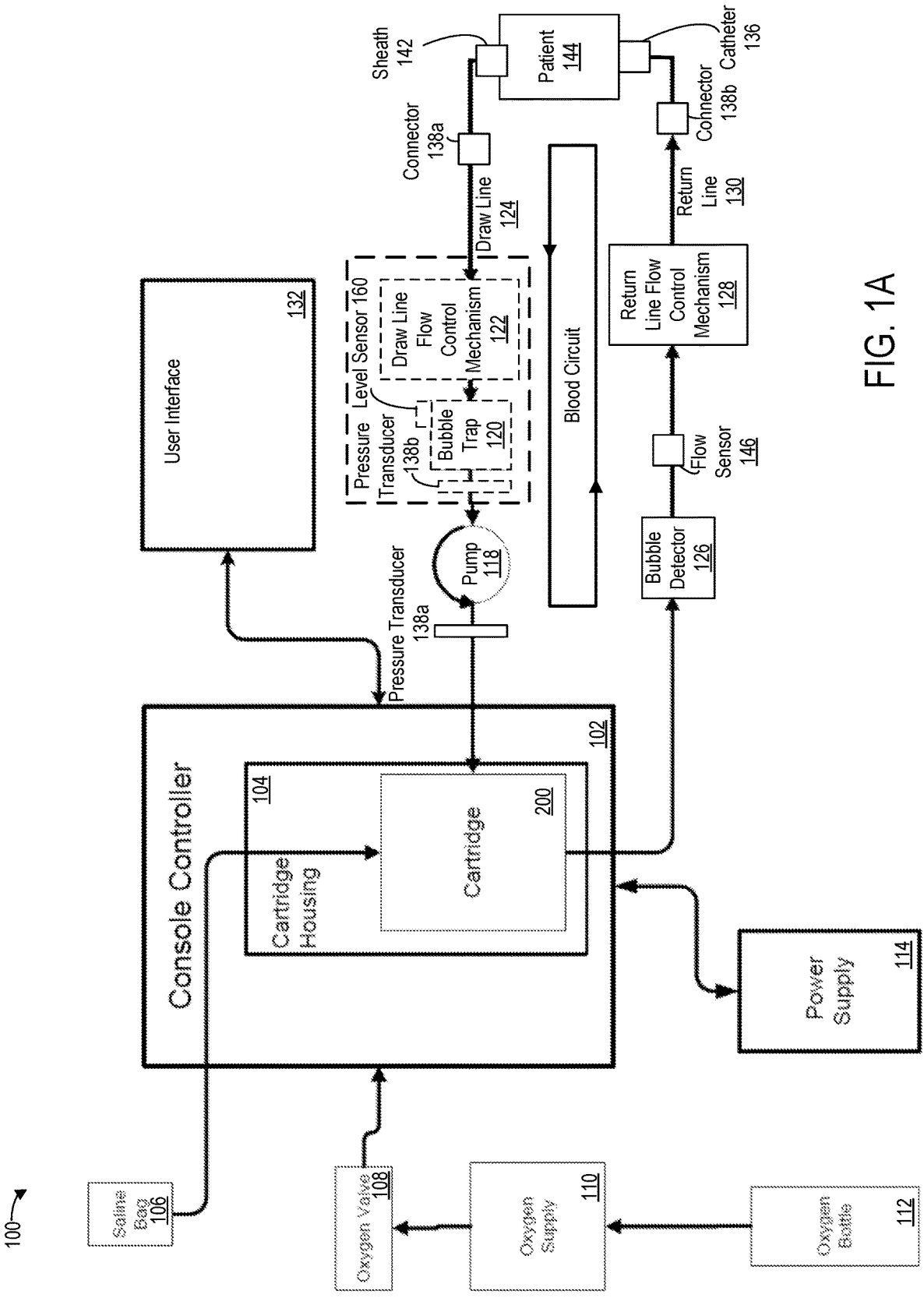
FIG. 1A is a diagram of an example gas-enrichment system for delivering gas-enriched blood within the vasculature of a patient.

The drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

The following disclosure describes systems and methods related to, and example embodiments of, gas enrichment therapy or supersaturated oxygen or gas therapy systems, methods and components. The systems permit gas-enrichment therapy, e.g., supersaturated oxygen (SSO2) therapy, to be provided to patients and controlled based on an analysis of one or more physiological parameters. SSO2 therapy refers to minimally invasive procedures for enriching oxygen content of blood through catheter-facilitated infusion of supersaturated oxygen-enriched physiological fluid (e.g., blood) or infusion of supersaturated oxygen-enriched liquid, such as saline, directly into a patient's blood vessel. These procedures generally are aimed at treating a patient who has suffered an acute myocardial infarction (AMI), but can be used for other conditions, including, but not limited to, peripheral vascular disease as well. There is a need for enhanced control of $SSO_2$ therapy based on feedback regarding changes in microvascular resistance, blood perfusion, tissue ischemia and infarct size in response to the $SSO_2$ therapy. The various feedback mechanisms described herein provide enhanced control of $SSO_2$ therapy and allow the caregiver and/or system to optimize $SSO_2$ therapy for improved patient outcomes.

The delivery system described in this document is configured to perform measurements of one or more physiological parameters to estimate a microvascular resistance in the patient. The delivery system uses the estimate of microvascular resistance to determine how to adjust control of delivery of gas-enriched blood to the patient. For example, the delivery system uses the estimate of microvascular resistance to determine how to titrate or control gas-enrichment therapy. Controlling gas-enrichment therapy may refer to a process of adjusting the delivery of gas-enriched blood or liquid either to increase the amount delivered or decrease the amount delivered over a period of time (e.g., several seconds to a several minutes) or increase or decrease the time of delivery or to stop or start delivery of the gas enriched blood or liquid, or to increase or decrease the amount of gas dissolved in liquid, which is then mixed with blood, in a precisely controlled way. For example, controlling delivery of the gas enriched blood or liquid can include titrating the delivery of the gas-enriched blood or liquid. The delivery system is configured for measuring the physiological parameters during delivery of the gas-enriched blood.

The delivery system may be configured for real-time or near-real-time control of the delivery of the gas-enriched blood or liquid (e.g., real-time control loop) for titrating or controlling the delivery of the gas-enriched blood or liquid to the patient based on the measured or estimated parameters. Real-time in this context refers to an instant or nearly instant generation of a control signal in response to receiving data from one or more sensors in communication with a controller of the delivery system. The control signal is generated with minimal delay, allowing for processing latencies and/or communication latencies inherent to measuring the physiological parameter values and processing the measured data. Real-time therefore refers to processing the measured parameter values as the data are received at the processor rather than storing the measured values for use in processing at a later time. For example, the delivery system can continually update a value in a sensor buffer representing the most recent measurement of the physiological parameter that is available to the controller for processing.

FIG. 1A is a diagram of an example gas-enrichment and delivery system 100 for delivering gas-enriched blood within the vasculature of a patient. The delivery system 100 can enable enrichment of a bodily fluid (e.g., blood) with a dissolved gas or gas-enriched liquid. As an example, the delivery system 100 creates a gas-enriched blood by enriching a patient's blood with a gas-enriched liquid, e.g., oxygen-enriched liquid, in an extracorporeal gas-enrichment and control system including a controller 102 and a cartridge 200. Gas-enriched blood, e.g., oxygen-enriched blood or supersaturated oxygen (SSO$_2$) enriched blood, is delivered to a patient 144, e.g., to a target region or localized region in the patient, thereby increasing oxygen in the blood of the patient and diffusion of oxygen into tissue to treat ischemic (oxygen-deprived) tissue, e.g., in the heart of a patient who has suffered a myocardial infarction. In some implementations, one or more objects described herein may be optional. In some implementations, one or more objects described herein in relation to FIG. 1A may be optional (including, but not limited to one or more of the bubble trap 120, draw line flow control mechanism 122, and/or pressure transducer 138*b*,). For example, objects that are represented by dashed lines may be optionally included in the system 100.

In certain implementations, oxygen-enriched liquid or solution, e.g., supersaturated oxygen liquid or solution, may include liquid having a dissolved O$_2$ concentration of 0.1 ml O2/ml liquid (STP) or greater or 0.1-6 ml O2/ml liquid (STP) or 0.2-3 ml O2/ml liquid (STP) (e.g., without clinically significant gas emboli). When such supersaturated oxygen liquid or solution is mixed with blood, the resulting blood may be referred to as supersaturated oxygen-enriched blood. In certain implementations, the system 100 may deliver an infusion of supersaturated oxygen-enriched blood having an elevated pO$_2$ in a target range of 400 mmHg or greater or 600-1500 mmHg or 760-1200 mmHg or around 1000 mmHg.

In one example, supersaturated oxygen-enriched blood may have a pO2 of 760-1500 mmHg when a source blood delivered to the gas enrichment system for mixing with a supersaturated oxygen liquid or solution has a minimum pO$_2$ of 80 mmHg, the blood flow rate is 50-150 ml/min, the SSO2 saline flow rate is 2-5 ml/min and the dissolved O$_2$ concentration in saline is 0.2-3 ml O2/ml saline (STP).

In another example, where the source blood is below 80 mmHg, the treatment objective may be to boost the blood pO2 to above 80 mmHg, so the system 100 may deliver an infusion of supersaturated oxygen-enriched blood having a pO2 level of 80 mmHg or greater or 80-760 mmHg.

The delivery system 100 is configured to perform real-time or near real-time measurements of regional myocardial blood pressure and/or flow and to use those measurements to provide feedback to optimize said gas-enrichment therapy, such as by titrating or controlling delivery of the gas-enriched blood. The delivery system includes one or more sensors for measuring a physiological parameter, e.g., pressure and/or flow. The measured physiological parameter is used to estimate microvascular resistance in the patient, as described in relation to FIG. 1B. For example, a reduction in microvascular resistance indicates a reduction in microvascular obstruction, which may result in a reduction in the size of an infarct, e.g., in the heart. In some implementations, the delivery system 100 estimates microvascular resistance, by using an index of microcirculatory resistance (IMR), to determine how to adjust delivery of gas-enriched blood in real time or near real time. IMR may include a pressure-temperature sensor guidewire-based measurement, performed during cardiac catheterization, of the minimum microcirculatory resistance in a target or localized microvasculature region, for example, near the coronary artery. Generally, IMR is correlated to microvascular obstruction (MVO), vascular blood flow, wall motion abnormality, left ventricular ejection fraction (LVEF), and myocardial viability.

Delivery of gas-enriched blood to the patient may result in a reduction in microcirculatory resistance, which results in a reduction in MVO, which results in an improved perfusion in the microvasculature and tissue. An effect of the delivery of gas-enriched blood and resulting reduction in IMR and MVO, may include a reduction in the size of an infarct. An infarct includes a small, localized area of dead tissue resulting from failure of blood supply in the vasculature of the patient. Therefore, a reduction in IMR, and a resulting increase in perfusion and blood supply to the infarct area, may be indicative of a reduction in infarct size.

As stated above, the delivery system 100 is configured for controlling gas-enrichment therapy in a patient by enriching a liquid with gas to form a gas-enriched liquid and to mix the gas-enriched liquid with blood to form gas-enriched blood. A pump 118, subsequently described in further detail, is configured to pump blood to and from the gas-enrichment system to and from the patient through a plurality of fluid conduits fluidly coupled to the gas-enrichment system. At least one sensor (e.g., described in relation to FIG. 1B) is configured to measure one or more physiological parameters indicative of a microvascular resistance in a vasculature of the patient.

A controller 102 comprising a processor, a memory, and associated circuitry is communicatively coupled to the at least one sensor. The processor is configured to receive one or more signals corresponding to a measured value of the one or more physiological parameters from the at least one sensor. The processor of the controller 102 is configured to estimate, based on the measured value, the microvascular resistance in the vasculature of the patient. The estimated microvascular resistance may include an estimation or determination of whether microvascular resistance is increasing or decreasing, rather than an absolute value. However, an absolute value of microvascular resistance can be estimated. The controller 102 is configured to generate, based on the estimated microvascular resistance in the vasculature of the patient, an alert that alerts the caregiver to take some action or control signal for sending to the pump 118 for titrating or controlling an amount of the gas-enriched blood delivered to the patient or the duration of delivery. The processes for titrating or controlling the amount of gas-enriched blood are subsequently described in further detail.

The blood circuit includes the blood mixing chamber of the cartridge that receives blood from the patient 144 and where enrichment of the blood with gas-enriched liquid occurs. The blood circuit may also include an air trap 120 or bubble trap chamber. The blood mixing chamber and/or bubble trap 120 may include one or more level sensors 160, e.g., ultrasound sensors, for detecting the presence or absence of liquid in the respective chamber or trap. These sensors 160 may send signals for controlling the flow control mechanisms depending on the presence or absence of liquid. The blood circuit also includes the tubing between and among these chambers. The blood circuit of the delivery system 100 is connected to an intravenous catheter 136 which is insertable into the vasculature of a patient 144 to complete the blood circuit. Blood is removed from the patient 144, drawn into the cartridge of the delivery system 100, mixed with gas-enriched liquid, e.g., oxygen-enriched saline, in the blood mixing chamber and returned to the patient. The chambers of the blood circuit may include one or more chambers of the cartridge 200, and the bubble trap 120. A bubble detector 126 may also be provided for detecting air bubbles in the blood circuit.

In certain implementations, the delivery system 100 may include a console controller 102 cartridge housing 104, a user interface 132, a pump 118, a power supply 114, and an oxygen valve 108 and associated oxygen supply connector 110. The delivery system is configured to connect to several consumable items that are used as a part of the delivery system 100, including an oxygen bottle 112, fluid source 106 (or saline bag 106), a cartridge 200 and the catheter 136.

The delivery system 100 further includes a draw line 124 for drawing blood from a catheter 136 through a connector 138*a*. The draw line 124 may include a bubble trap chamber 120 and is configured to interface with a pump 118 and may be configured to interface with a first flow control mechanism, e.g., a draw line flow control mechanism 122 of the delivery system 100. Pressure transducers 138*a-b* may be located on either side of the pump 118 to measure pressure of blood flowing through the blood circuit, such as through the draw line 124, through the return line 130, or through each of the draw line and the return line.

The delivery system may include a flow sensor 146, for example on or near the blood circuit (e.g., on the return line 130) to measure the flow rate of the blood circulation in the blood circuit. For example, the flow sensor 146 can measure a number of milliliters per minute (mL/min) of gas-enriched blood delivered to the patient 144. In some implementations, the flow sensor 146 is positioned near the pump 118. In some implementations, the flow sensor is positioned near the return line 130.

The delivery system 100 includes a return line 130 for returning gas-enriched blood to the catheter 136 in the patient 144. The return line 130 may be connected through a bubble detector 126, and connected to the catheter via a connector 138*b*. The return line may be configured to interface with a second flow control mechanism, e.g., a return line flow control mechanism 128. As stated previously, a draw clamp or valve can be used to perform the functions of the draw flow control mechanism 122, and a return clamp or valve can be used to perform the functions of the return flow control mechanism 128. In some implementations, another mechanism for controlling or regulating flow of the blood in the blood circuit (e.g., to prevent blood flow and/or flow of room air or air bubbles) can be used to perform the functions of the draw flow control mechanism 122 or return flow control mechanism 128.

The catheter 136 is connectable to the delivery system 100. For example, the catheter 136 is a single-use consumable device that is used once before being discarded. The catheter includes a lumen for delivering gas-enriched blood to the patient 144. In the blood circuit, the draw line 124 may be connected (e.g., by connector 138*a*) to a sheath inserted into the patient 144 for drawing blood from the patient 144. The return line 130 may be connected (e.g., by connector 138*b*) to the catheter 136 to return blood to the patient 144. In some implementations, the catheter, which includes a lumen for delivery of the gas-enriched blood to the patient may be inserted through the sheath 142 positioned in the patient's vasculature. In this example, the return line 130 is connected to the catheter 136. The sheath includes a lumen for drawing blood from the patient 144, and the draw line 124 is connected to the sheath. Alternatively, the catheter may include a second lumen for drawing blood from the patient 144 so that the sheath 142 is not used, and so the catheter is configured for both returning and drawing blood from the patient 144. In this example, the draw line 124 and the return line 130 are connected to the catheter 136. The delivery system 100 is configured for use with different types of catheters. In another example, the sheath 142 includes a first lumen for connecting to the draw line 124 for drawing blood from the patient 144 and a second lumen for connecting to the return line 130 for returning blood to the patient.

To deliver gas-enriched blood to a patient 144, the delivery system 100 operates as follows. The delivery system 100 console 102 is connected to each other component of the delivery system. For example, the cartridge 200 is inserted into the cartridge housing 104 of the console 102. Tubing (e.g., the draw and return lines) extending from the cartridge and connecting the cartridge 200 to the catheter 136 is interfaced with the draw flow control mechanism 122, and/or return flow control mechanism 128, and pump 118 of the console. The cartridge and draw and return lines 124, 130 may be configured such that upon insertion of the cartridge into the cartridge housing, the tubing automatically self-aligns with the draw flow control mechanism 122 and/or return flow control mechanism 128, and pump. For example, the cartridge may have return and draw lines, which have a predefined orientation and shape that match with a corresponding shape or design in the cartridge housing and/or on the console. The predefined orientation and shape is such that upon insertion of the cartridge into the cartridge housing, the draw line and return line automatically align with and interface with the draw and/or return flow control mechanisms 122, 128, and the pump 118. The power supply 114 is connected to an external power source for providing power to the console 102. The oxygen supply 110 receptacle is provided an oxygen bottle 112 for providing the source of oxygen to the cartridge 200. The user interface 132 can indicate whether any of these consumables are missing from the delivery system 100 before or when delivery of the enriched blood to the patient is beginning.

Figure 1B:
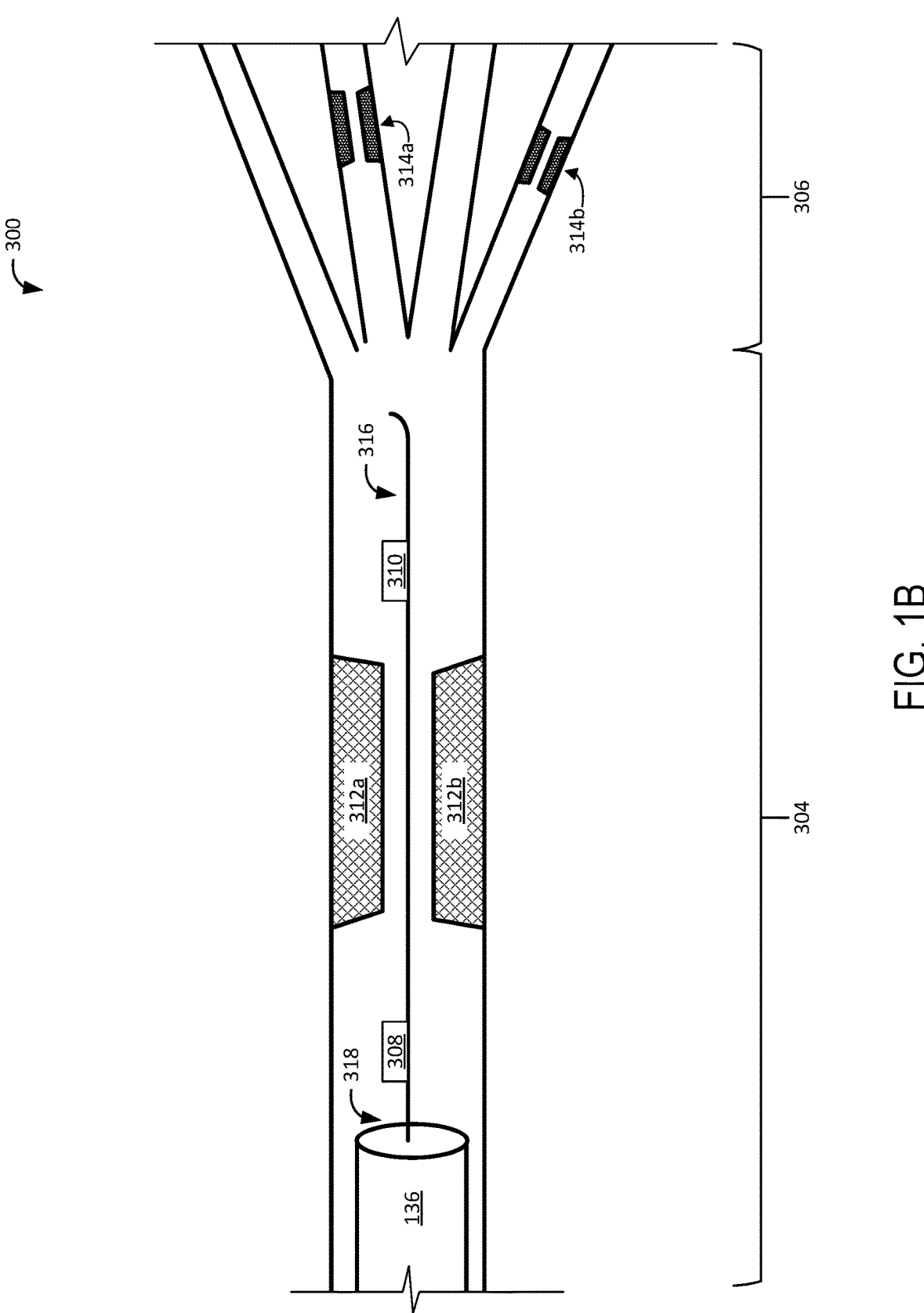
FIG. 1B is a diagram of an example catheter in the vasculature in the patient including sensors for measuring physiological parameter values.

Turning to FIG. 1B, a diagram of an example delivery catheter 136 for delivery of gas-enrichment therapy is shown in the vasculature 300 of the patient including sensors 308, 310 for measuring physiological parameter values to estimate the microvascular resistance in the patient. In the example of FIG. 1B, the vasculature 300 can include an epicardial vessel 304 and a microvasculature 306. Infarct areas 312*a-b* can exist in the epicardial vessel 304. Infarct areas 314*a-b* can exist in the microvasculature 306.

The catheter 136 includes a wire 316 that extends from a distal end 318 of the catheter 136 into the vasculature 300 of the patient. The wire 316 supports sensors 308 and 310. Sensors 308, 310 can be instances of a same type of sensor or different types of sensors. In an example, each of sensors 308, 310 includes a pressure sensor configured to measure blood pressure in the vasculature 300 of the patient. The two pressure sensors 308, 310 can provide a pressure differential (Δp) value for a region 304 of the vasculature around infarct areas 312a-b, e.g., the sensors may record a blood pressure drop across the infarct areas 312a-b. In some implementations, the sensors 308, 310 are configured for measuring a relative difference in blood flow in the myocardium of the patient. When using wire-based IMR to estimate microvascular resistance, blood flow data is derived via the thermodilution method. Temperature sensors (e.g., thermistors) located at the proximal and distal end of the wire may be utilized to measure the change in cold saline temperature. For example, a pressure sensor on the distal end of the wire can act as a distal thermistor, while a pressure sensor on the proximal shaft of the wire serves as a proximal thermistor. Accordingly, a mean transit time ($T_{mn}$) of room-temperature saline injected into a coronary artery can be determined from a thermodilution curve. Using the known thermodilution technique, a correlation between the inverse of $T_{mn}$ ($1/_{Tmn}$) and absolute coronary flow is shown. Absolute coronary flow$\approx 1/T_{mn}$. IMR$=\Delta p/(1/T_{mn})$. In general, IMR$=$pressure/flow.

In certain implementations, IMR (index of microcirculatory resistance) may be calculated using the mean distal coronary pressure Pa and myocardial flow, which is equal to $1/T_{mn}$, where $T_{mn}$ is mean transit time. The minimal achievable resistance is calculated by making the measurement during maximal hyperemia. Accordingly, IMR$=$Pd$/(1/$Tmn$)$ or Pd*Tmn at maximal hyperemia. IMR can provide qualitative information about resistance to flow in the vasculature (e.g., regional microvasculature) after inducing hyperemia. A change in IMR over time in the direction of normal IMR would be a desirable result and a measurable effect of gas-enrichment or $SSO_2$ therapy.

In some implementations, the sensors 308, 310 include flow sensors configured to measure the flow of blood directly in the patient. The flow sensors can include electromagnetic, mechanical, or ultrasonic flow sensors.

The sensors 308, 310 may send pressure measurements (or measurements of another physiological parameter) to the controller 102 for estimating the microvascular resistance in the microvascular region 306. The estimate can include determining a ratio of a change in pressure to the flow. In some implementations, at least one sensor 308, 310 includes a pressure sensor. The physiological parameter includes a pressure or pressure change of blood in the vasculature 300 of the patient. In some implementations, at least one of the sensors 308, 310 includes a flow sensor. The physiological parameter thus includes a flow rate of blood in the vasculature of the patient.

In some implementations, the wire 316 is positioned on or near a distal end 318 of the delivery catheter 136. In some implementations, the one or more sensors 308, 310 are positioned directly on the body of the catheter 136. The wire 316 can extend through a lumen of the catheter 136 out of the distal end 318 of the catheter. In some implementations, the wire 316 extends along the catheter 136 shaft on an exterior of a catheter lumen.

In some implementations, the wire 318 is positioned on a separate probe that is not directly attached to the delivery catheter 136. In some implementations, a second, separate catheter is used to support the one or more sensors 308, 310. In such an example, the catheter 136 is not the delivery catheter, but a second, different catheter, and the delivery catheter is not shown.

The one or more sensors 308, 310 are configured to send data to the controller 102 which can display feedback on the user interface 132 responsive to receiving the data from the sensors. The feedback that is displayed on the user interface 132 can include a display of blood pressure values, flow rate values, an estimate of the microvascular resistance, an estimate of the change in microvascular resistance in the vasculature 300 over time, a rate of delivery of the gas-enriched blood (e.g., a titration value), a rate of delivery of the gas-enriched liquid e.g., saline, a pump speed and direction, and so forth. As subsequently described in additional detail, the feedback displayed by the user interface 132 can include a time series showing a sequence of measurements. In some implementations, the feedback can include a diagram or graph that is continually or intermittently updated as new data are acquired and the estimate of microvascular resistance is updated. For example, the estimate of microvascular resistance can be graphed in relation to time.

The data from the sensors 308, 310 is sent to the controller either automatically and directly or through action of a user. For example, for a non-invasive imaging modality (subsequently described), the feedback may be input into the user interface by a user. In some implementations, a tomographic measurement signal may be sent directly to the controller 102. In some implementations, the data are sent from sensors 308, 310 over the wire 316 to the controller 102, which is connected either directly to the wire 316 or indirectly to the wire through a catheter hub.

Data generated from the sensors 308, 310 are used for controlling delivery of the gas-enriched blood or liquid to the vasculature of the patient. In some implementations, the $SSO_2$ delivery includes a direct injection of gas-enriched liquid to the blood in the vasculature of the patient. In some implementations, the $SSO_2$ delivery includes mixing the blood of the patient with the gas-enriched liquid in a mixing chamber outside of the patient, and delivering the gas-enriched blood to the patient using the catheter 136.

The delivery system 100 is configured to control delivery of gas-enrichment therapy based on the feedback of sensors 308, 310. In some implementations, the delivery system 100 is configured to augment blood flow. In some implementations, the delivery system 100 is configured to increase a concentration of oxygen in the gas-enriched liquid/blood delivered to the patient. In some implementations, the delivery system 100 increases or decreases an amount of gas-enriched blood/liquid to the patient, either by increasing or decreasing the flow rate of gas-enriched blood delivery or by increasing or decreasing the duration of gas-enriched blood delivery.

Generally, the controller 102 is configured to adjust gas-enriched liquid or blood delivery based on a target value. The target value generally includes a target estimate for microvascular resistance. However, the target value can include a target amount of delivered gas-enriched liquid or blood, in which the estimate of microvascular resistance is used as a value from which the target amount of delivered liquid or blood is determined. Generally, a physician (or other user) can set the target value and control operation of the delivery system 100.

In some implementations, the delivery system 100 is configured to display a coronary flow reserve (CFR), which includes a maximum increase in blood flow through the coronary arteries above the normal resting volume is global flow. The delivery system 100 measures a flow normal and flow hyperemia vasodilate in vessels and finds a ratio of these values. In some implementations, the delivery system 100 determines an epicardial fractional flow reserve (FFR), which is measured by a pressure probe (e.g., sensor 308, 310) into the coronary artery 304. A pressure drop between proximal and distal ends of the artery 304 is determined. These values can be displayed on the user interface 134 along with any other operational values of the delivery system 100 described herein.

The controller 102 of the delivery system is configured to determine a change in the microvascular resistance of the vasculature 300 of the patient over time. In response to this determination, the controller generates an alert or control signal for titrating or controlling the gas-enriched blood delivered to the patient. The controller 102 is configured to send a control signal to the pump 118 during operation of the pump for delivery of the gas-enriched blood to the patient. The controller 102 causes, based on sending the control signal, the pump 118 to increase a pump speed or reduce a pump speed to increase or reduce the amount of the gas-enriched blood delivered to the patient. In some implementations, titrating or controlling the amount of the gas-enriched blood delivered to the patient includes determining by the controller 102 that a change in the value of the pressure or flow rate from the sensors 308, 310 represents a reduced microvascular resistance in the vasculature of the patient. In certain implementations, the controller may estimate microvascular resistance by determining the IMR over a period of time and consider the reduction in IMR over that period of time. If the IMR is still decreasing, that may indicate that more gas-enrichment or SSO2 therapy is needed. If IMR has reached a plateau, that may indicate that a maximum benefit of the therapy has been reached, and therapy can be stopped.

In response to determining that the IMR has reached a plateau, or that the change in the value represents a reduced microvascular resistance, the controller 102 can generate a control signal that is configured to cause a reduction in the amount of the gas-enriched blood delivered to the patient or a reduction in the amount of oxygen dissolved in liquid, which is mixed with blood to form the gas-enriched blood. Alternatively, the controller my generate an alert in response, which tells the caregiver to take the necessary action to reduce the amount of the gas-enriched blood delivered to the patient or reduce the amount of oxygen dissolved in liquid.

In some implementations, titrating or controlling the amount of the gas-enriched blood delivered to the patient includes determining, by the controller 102, that a change in the value of the flow or pressure change represents an increased microvascular resistance in the vasculature 300 of the patient. In certain implementations, the controller may estimate microvascular resistance by determining the IMR over a period of time and consider the increase in IMR over that period of time. If the IMR is still increasing, that may indicate that more gas-enrichment or SSO2 therapy is needed. If IMR has reached a plateau, that may indicate that a maximum benefit of the therapy has been reached, and therapy can be stopped.

The controller 102, in response to determining that the IMR is increasing, or that the change in the value represents the increased microvascular resistance, can generate a control signal that is configured to cause an increase in the amount of the gas-enriched blood delivered to the patient or an increase in the amount of oxygen dissolved in liquid, which is mixed with blood to form the gas-enriched blood. Alternatively, the controller my generate an alert in response, which tells the caregiver to take the necessary action to increase the amount of the gas-enriched blood delivered to the patient or increase the amount of oxygen dissolved in liquid.

The control of the gas-enriched blood delivery is performed in real-time or near-real time. The delivery of the gas-enriched blood to the patient is not paused during measurement of the one or more physiological parameters. The measurement of the one or more physiological parameters represents a contemporaneous status of the patient for the delivery of the gas-enriched blood to the patient. Generally, the real-time or near-real time comprises processing, by the controller, data received from the one or more sensors as soon as the data are available to the controller and generating the control signal or alert based on the processing, as previously described in order to titrate or control the gas-enrichment therapy based on said feedback.

The controller 102 is configured to control gas-enriched blood delivery over time. The controller 102 receives one or more signals corresponding to a measured value of the one or more physiological parameters from the sensors 308, 310. The controller 102 can receive a series of measured values of the pressure values or flow values from the sensors 308, 310 over time. The series of measured values corresponds to a period of time during delivery of the gas-enriched blood to the patient. The controller 102 determines, based on the series of measured values, whether the value of the pressure or flow (or microvascular resistance) is increasing or decreasing over time. The controller 102 generates the control signal that is configured to increase or reduce the amount of the gas-enriched blood delivered to the patient based on the time series of values. For example, if the pressure values are increasing over time, the controller may titrate the gas-enriched blood delivery up to deliver more oxygen to the vasculature 300. For example, if the pressure values are decreasing over time, the controller may titrate the gas-enriched blood delivery down to deliver less oxygen to the vasculature 300.

The controller 102 can titrate or control the gas-enriched blood delivery based on other data in addition to or instead of the data from sensors 308, 310. For example, the controller 102 is configured to receive angiogram data representing the patient for one or more time periods contemporaneous with delivery of the gas-enriched blood to the patient. The angiogram data can include images of the vasculature 300 of the patient that shows indications of infarct regions 312*a*-*b*, 314*a*-*b*. Infarct regions 312*a*-*b*, 314*a*-*b* include blockages in the vasculature. Generally, infarct size, expressed as a percentage, is determined by dividing the sum of infarct areas from all sections by the sum of vessel cross section area from all sections of the vasculature. The images provide additional context to the pressure and/or flow data from sensors 308, 310 for estimating microvascular resistance. In certain implementations, angio-IMR flow can be derived/estimated from an angiogram's TIMI frame count. In certain implementations, angio-IMR may be estimated or calculated from the angiogram data, e.g., using FlashAngio™ software by Rainmed™.

The controller 102 is configured to generate, based on the angiogram data, and/or the microvasculature resistance or IMR estimated from the angiogram data, the control signal or alert to increase or reduce or stop (e.g., titrate or control) the amount of the gas-enriched blood delivered to the patient. In certain implementations, the control signal or alert may be generated in real time or near real time.

In certain implementations, the system 100 may receive imaging data e.g., angiogram imaging data, representing the vasculature of the patient, and estimate, based on the imaging data and/or measured values of the sensor, a microvascular resistance, e.g., IMR, in the vasculature of the patient to provide feedback for controlling an amount of the gas-enrichment therapy.

Returning to FIG. 1A, once each of the components of the delivery system are connected, including the cartridge 200, pump 118, bubble detector 126, return flow control mechanism 128, and catheter 136, and optionally the draw flow control mechanism 122 and bubble trap 120, the delivery system 100 is ready for use. The blood circuit is shown with arrows representing the direction of blood flow during operation of the delivery system 100, where blood is pulled from the catheter 136 through the draw line, through the cartridge and blood mixing chamber where it is mixed with gas-enriched liquid and the resulting gas enriched-blood is returned to the catheter via the return line.

Prior to operation, a priming process is run which causes the blood circuit to be filled or substantially filled to a threshold level with blood such that there is no room air and/or air bubbles in the blood circuit, which could travel to the patient 144. For example, the draw line 124 and return line 130 are filled with blood. For example, the bubble trap 120 and pump 118, and the tubing connecting the various elements of the blood circuit, are filled with blood. The blood mixing chamber of the cartridge 200 is filled with blood, e.g., to a threshold level.

Room air and/or air bubbles from each of the elements of the blood circuit is vented from the respective elements, as subsequently described. The bubble detector 126 is configured to detect any bubbles present in the blood circuit during operation of the delivery system 100 and can send a signal resulting in the closing of the return flow control mechanism 128 if room air and/or air bubbles are detected in the blood circuit. This prevents air bubbles from reaching the patient 144 at the catheter 136. The bubble detector 126 can include an ultrasonic sensor, infrared (IR) sensor (e.g., a photogate), or other such mechanism for detecting air or bubbles in line. For example, the bubble detector 126 can include an IR sensor that senses an IR beam sent through the fluid of the blood circuit. An air bubble in the fluid distorts the beam, which can be detected by an IR sensor.

The delivery system 100 may be configured to control the oxygen levels in the blood and/or tissues of the patient 144 by controlling the oxygen levels in the supersaturated oxygen liquid or solution, (e.g., targeting a dissolved $O_2$ concentration in saline of 0.1 ml O2/ml liquid (STP) or greater or 0.1-6 ml $O_2$/ml liquid (STP) or 0.2-3 ml $O_2$/ml liquid (STP) and/or the flow rate of the supersaturated oxygen-enriched blood delivered to the patient 144, e.g., by controlling the speed of the pump to achieve a target blood flow rate of 10-500 ml/min, 30-300 ml/min or 50-150 ml/min. The system 100 may be configured to titrate oxygen into liquid e.g., saline, to be mixed with blood and adjust the oxygen level and/or blood flow rate The concentration of oxygen delivered, and/or the blood flow rate may be modulated during treatment based on feedback from one or more sensors measuring one or more physiological parameters indicative of a microvascular resistance in a vasculature of the patient and estimation of the microvascular resistance based on the measured physiological parameters.

As discussed herein, one or more blood pressure sensors may be used to measure blood pressure values in blood from a patient receiving gas-enrichment therapy. A processor of the controller receives signals from the blood pressure sensor, which correspond to the measured values of blood pressure and changes in blood pressure. The processor may compare the measured blood pressure to a target range of blood pressure, e.g., blood pressure in a healthy individual. The processor may generate an alert, e.g., through the user interface, that indicates the blood pressure or a change in blood pressure. The measured blood pressure or change in blood pressure may be indicative of the microvascular resistance in the vasculature of the patient. The processor may control the gas enrichment system by modifying one or more saline or blood parameters in the gas-enrichment system to optimize therapy based on the blood pressure feedback.

A change in blood pressure may be indicative of a change in blood flow in myocardial tissue in response to the gas-enrichment therapy. The gas-enrichment therapy, e.g., SSO2 therapy, provides a high concentration gradient of O2 that enables increased diffusive transfer to ischemic areas of myocardium. This diffusive transfer of O2 to areas most in need does not depend on blood flow and thus O2 can easily access the endothelial cells of capillaries suffering from edema (swelling). SSO2 therapy is able to reverse this edema response in the microvasculature and restore flow, nurturing surrounding heart tissue with oxygenated blood.

In addition to the wire with pressure sensors discussed above, another example sensor for measuring an arterial pressure of the patient's blood includes a pressure sensor positioned in or coupled to the catheter. The catheter may be connected to a fluid-filled system or pressure tube, which is connected to an electronic pressure transducer and/or pressure monitor. A change in detected blood pressure may be indicative of improved perfusion and/or restored flow in ischemic tissue as a result of the SSO2 therapy. The therapy may result in improved heart function. In certain implementations, the processor may control the delivery of SSO2 therapy based on the arterial pressure feedback.

In certain implementations, feedback may be based on a measured blood pressure waveform. A change in a waveform reflection pattern may be detected. In one example, changes in the reflection pattern of the normal pulsatile waveform of the patient's blood pressure may be detected or measured. In another example, a pulsatile flow may be created (for more fine tuning), and changes in the reflection patter of the created pulsatile waveform of the patient's blood pressure may be detected or measured. In either example, the pulsatile waveform may be analyzed for information, such as the relative magnitude and the timing of the secondary peak identified in that waveform.

The user interface 132 is configured to display operational data and/or patient data on the user interface in a configuration that allows a user to determine a status for the $SSO_2$ liquid and gas-enriched blood delivery to the patient 144. The user interface 132 shows a current operational status of the delivery system 100.

These values can be stored as a time sequence of data entries or log entries in an operational log. The user interface may include a visual representation of the operational log, the visual representation including operational data specifying how the delivery system 100 is performing during delivery of the enriched blood to the patient. For example, the delivery system 100 logs sensor readings and IMR during delivery and generates an alert or report indicating whether the delivery of gas-enriched blood should be titrated or controlled. In some implementations, the delivery system 100 can send logged data to remote, networked storage (e.g., in cloud storage) for access from one or more networked devices.

In some implementations, various data elements are logged during the delivery process. For example, the duration of delivery can be logged. Each time a checkpoint is reached, a time stamp associated with the checkpoint is saved. Checkpoints can include completion of the delivery process, indication of titration of the delivery of gas-enriched blood, indication of values of one or more physiological parameters such as pressure or flow rate, a visualization of an estimate of the microvascular resistance, or any other data of interest during the delivery process. The values of sensors, such as the level sensors, pressure sensors and temperature sensors, can be stored at given instances in time. The operational values of devices on the blood circuit can be monitored, such as how fast the pump is operating, blood levels in the blood mixing chamber or bubble trap, when one or more flow control mechanisms 122, 128 are actuated, and so forth. These data provides information to determine whether an issue is occurring during delivery of the gas-enriched blood.

In some implementations, the delivery system 100 may include a processor, a memory, and associated circuitry coupled to the one or more sensors for detecting physiological data. The physiological data is collected and/or stored in the system for retrospective, current or other review. The delivery system 100 is configured to generate log entries for the operational data (e.g., delivery data). The log entries may be displayed on the user interface 132. In certain implementations, the log entries can each be structured messages that include particular values associated with the operation of the delivery system 100, generated from data messages. In some implementations, a data message (also called a log message) represents an instant snapshot of the operational data. For example, a data message can include treatment data or current pressure, flow or microvascular resistance values at a given time (e.g., associated with a time stamp). In some implementations, a data message can include data representing a treatment period or system mode of the gas-enriched liquid treatment for the patient 144 in a structured log entry. The data messages are stored in a digital format that enables streaming of the data messages to a remote system. The remote system is configured to quickly extract the values representing the patient data and the operational data of the delivery system 100 and display a representation of these data on a local or remote user interface. For example, data messages can be formatted for streaming to an operator or nurse's station from a hospital room. In some implementations, data messages can include warnings or alerts that prompt intervention from a user of the remote system. In some implementations, the data messages can be stored in a structured format that facilitates searching and retrieving of operational data for the patient 144 for operation of the delivery system 100 during SSO$_2$ delivery.

In some implementations, the log entries can each be structured messages that include particular values associated with the operation of the delivery system 100, generated from data messages. For example, the data messages can indicate a current snapshot of the operation of the delivery system 100. In this case, the values of the data message include a list of operational values and/or physiological values. The operational values and/or physiological values can be parsed from the data messages (e.g., by a remote device) and used to populate a screen or display of a remote computing system. For example, the delivery system 100 can transmit a stream of data including the data messages to a remote system for remote monitoring of the operation of the delivery system 100. In some implementations, the processor is configured to stream digital output data having the patient data and the operational data to a remote server. In some implementations, operational and patient data may be transmitted or streamed in real time or near real time via a wired, RS-232 streaming output on the system console to a remote processor or computer, e.g., to an EMR data hub or hospital hub. In some implementations, operational and patient data may be transmitted or streamed in real time or near real time over a WiFi communications, Bluetooth, cellular, USB or other wireless connection or link.

The data messages can include summary data. For example, log entries can include data representing a summary of operational and/or physiological data for a time period (e.g., pre-titration data, titration data, and post titration data). Each log entry may form all or a portion of the operational log, which provides an overall summary of the operation of the delivery system 100. The operational log allows a medical service provider to quickly review the summary of the operation of the delivery system 100. The operational and physiological data, e.g., data messages, log entries, operational log and/or other data, stored by the system processor or an accessary to the system or data module, coupled to the system console, may be stored on volatile or non-volatile memory. The log entries can be visually represented on the user interface 132.

Data messages may provide instant values of operational data of the delivery system 100 and the physiological data. Log entries may represent data gathered over time and can be part of a system and/or patient profile. For example, the operational log and the log entries can be stored in electronic medical records (EMR).

In some implementations, the log entries of the operational log are transmitted to a remote device (such as a data hub in a hospital). The delivery system 100 sends the data including the log entries to the remote device in one or more different ways. The delivery system 100 sends the log entries data to a remote device in response to a trigger. For example, the delivery system 100 can send the log entries to the remote device once titration or control of delivery of the gas-enriched blood is completed. In some implementations, the delivery system 100 sends the operational log data once all treatment is completed. For example, when the cartridge 200 is removed or the pump 118 is powered off, the controller 102 can determine that treatment is completed and send the log entry data to the remote device.

In some implementations, the delivery system 100 sends the operational log data to the remote device upon detecting a fault, such as a bubble trap 120 fault, a catheter 136 fault, a patient blood pressure or microvascular resistance value failing a threshold, etc. The operational log data can be analyzed (e.g., by a user) to determine why the fault occurred and/or to determine whether operation of the delivery system 100 is adversely impacted by the fault. This enables the user to take corrective measures immediately (e.g., replacing a bubble trap 120, fixing a fluid leak, etc.) to ensure that treatment of the patient 144 is not compromised.

In some implementations, the delivery system 100 sends the operational log data without a trigger. For example, the delivery system 100 can send the log entry data to the remote device periodically (e.g., once per minute, once per hour, etc.).

In an aspect, the delivery system 100 links the log entries related to operation together in a structured format. For example, a key value can be stored with each log entry. The entire log of the operation of the delivery system 100 can be retrieved by referencing the key value.

The delivery system 100 can generate one or more alerts to indicate a status of one or more components of the delivery system 100. The alerts can be generated based on the operational log data or data of the data messages. The alert can be generated for presentation on a user interface 132 of the delivery system 100. The processor may send the alert to one or more other computing devices, such as computing devices associated with a health care provider of the patient 144. In an aspect, a user interface is configured to communicate with the processor, wherein the data representing the alert indicating whether a fault has occurred, priming has initiated/completed, or any other relevant aspect of the operation of the delivery system 100 that satisfies a notification rule causes a notification to be displayed on a user interface. The user interface may be coupled to the console via a wire or wirelessly (e.g., the user interface may be a portable tablet or remote computing device)

The alert may indicate that there is a fault or error in operation of the delivery system 100. The alert provides an indicator for a health care provider to investigate the operation of the delivery system 100, such as to investigate whether any faults have occurred. The alerts may indicate that titration of the delivery of the gas-enriched blood has completed, that there is a pressure over value in the blood circuit, that room air and/or air bubbles have been detected, etc.

In some implementations, the processor generates the alert to cause one or more devices to perform an action. For example, feedback can be presented to a healthcare provider, such as an audio cue, visual presentation, and so forth. The alert can cause a device to contact a healthcare provider (e.g., place a phone call or page to a physician, nurse, etc.). The alert can cause a device to display particular data about the delivery process or performance of the system, or data about the patient 144, such as a presentation of blood pressure or microvascular resistance values over a given treatment period. The alert can cause a device to update a health record associated with the patient 144 or cause the device to retrieve a health record associated with the patient for further analysis. In certain implementations, the processor of the system may be configured to determine if the alert is a real time alert or recorded for retrospective review. If it is a real time, the processor determines whether to display the alert on the user interface, transmit the alert in an information chain, or send the alert data to a third-party monitor. An example route is to send the alert to a physician or nurse's cell phone.

The alert may open a cell phone-based application or open an Internet-based application. From either application the physician or nurse could see the alert plus other relevant data that may have been transmitted. The alert may include a hospital specific patient identifier, but otherwise be invisible as to the identity of the patient 144, unless the physician or the hospital has added the patient's name to either the application on their phone or to the Internet. The alert may include a non-patient specific identifier such as a bed number. Additionally, the physician would have the opportunity to take actions in response to receiving the alert. This might include triggering a phone call to the ICU desk or marking that the physician has seen the alert. Changing the duration or range of a monitored value would allow the user to set a duration so that a transient spike would not trigger the alert. In the case of adjusting the time and/or duration of the alert, such an adjustment may only affect the notification to that specific person.

A dual alert to a nurse or physician might have different alert ranges and actions. The described features may put the user, e.g., physician in complete control. For example, the first point of control may be at the bedside, where the alert ranges may be set. The second point of control may be at the receiving application or website where the user may adjust nominal settings, e.g., for "tones". As such, two or more triggers may be established: the first is to "send" the alert from the machine into the network to the receiving device; and the second is the action that the receiving device takes upon receiving the alert. A scheduling feature may also be provided that allows for the transfer data from one physician going off shift to another coming on shift. A response tree may be provided that requires an acknowledgement that the alert has been seen or transferred from one physician to another. For example, a first doctor is given 5 minutes to acknowledge receipt of the alert, and if no acknowledgment is made, the alert is sent to another physician or nurse. In certain implementations, one or more of the various alerts or alert parameters described herein may be customized by the user. Multiple options for alert delivery, e.g., device display, nurse's station, EMR, cell phone, etc. may be set. An alert for thermoregulatory activity of a patient 144 may include other forms. For example, a color scale or audible alert may be output via the user interface to provide a value indicative of patient activity.

In some implementations, a medical service provider can query the delivery system 100 to obtain the operational data. The query can request particular data, such as what the battery status is, determine whether titration of gas-enriched blood was successful, and so forth.

In some implementations, a controller is configured to store digital output data representing the delivery process in a data store. The controller is configured to detect that a trigger condition of the delivery process is satisfied. For example, the trigger condition can include completion of all or a portion of the delivery process. In some implementations, the controller, in response to detecting that the trigger condition is satisfied, transmits the digital output data to a remote device in real time or in near real time, e.g., during or after the delivery of gas-enriched blood by the delivery system.

In some implementations, the digital output data includes a predefined format that enables the digital output data to be streamed to a remote device. The delivery system can include a transmitter configured to transmit the digital output data to the remote device. In some implementations, the predefined format is configured to enable the remote device to parse the digital output data for displaying the physiological data and/or the operational data upon receiving the digital output data. In some implementations, the process includes streaming the digital output data over a WiFi communications, Bluetooth, cellular, or other wireless connection or link or USB. In some implementations, the process includes transmitting the digital output data over a wired connection.

Figure 2:
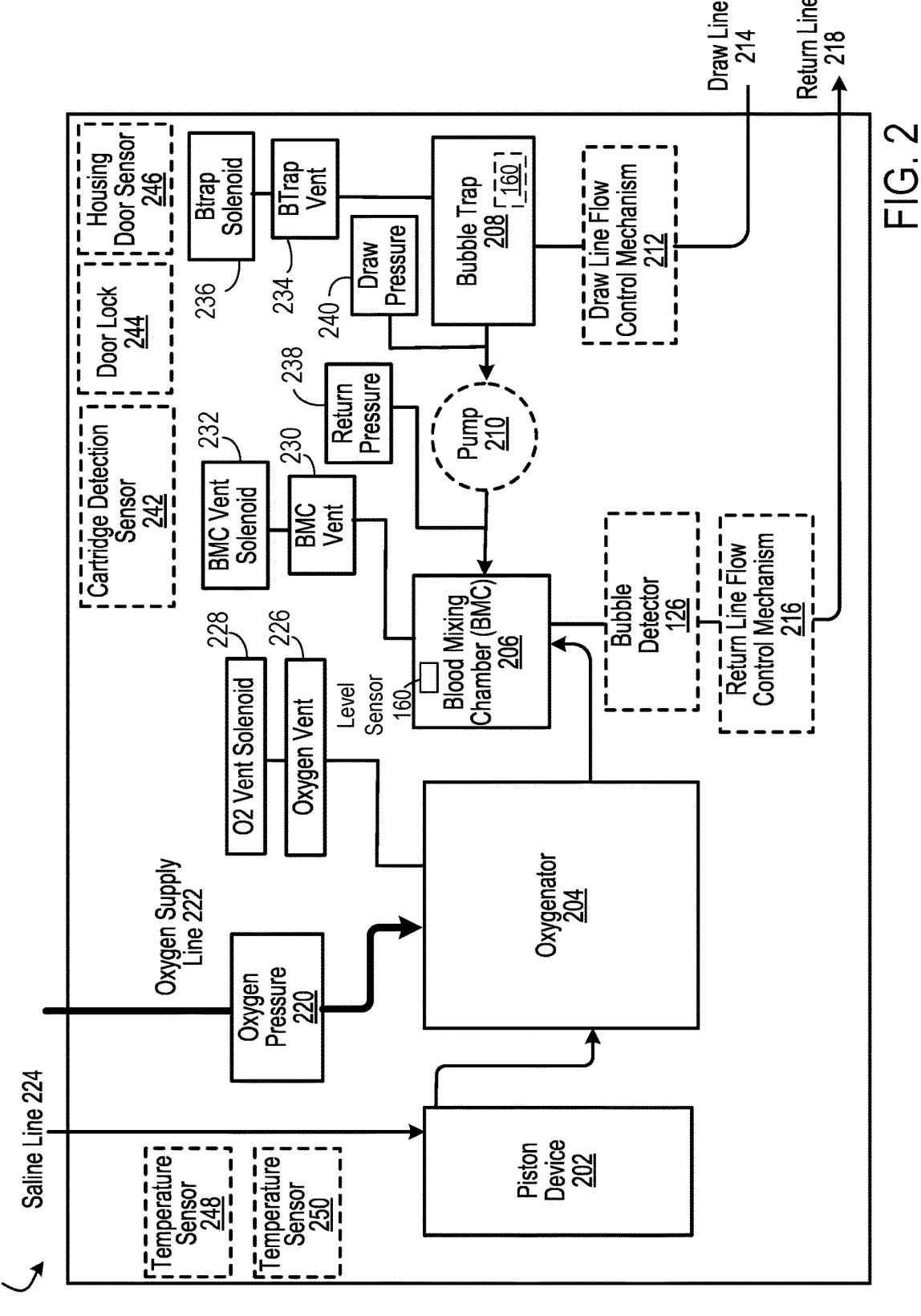
FIG. 2 is a diagram of a portion of the system of FIG. 1A-1B including a cartridge.

FIG. 2 is a diagram of an example of a portion of the system of FIG. 1 including the cartridge 200. In this example, the cartridge 200 includes a fluid supply chamber (piston device 202), a gas enrichment chamber (an oxygenator 204), and a blood mixing chamber 206. In some implementations, the cartridge 200 may also include a bubble trap 208, and at least a portion of the draw line 214 tubing and the return line 218 tubing. In FIG. 2, the pump 210 is similar to pump 118, the draw line 214 is similar to draw line 124, the return line 218 is similar to return line 130, and the bubble trap 208 is similar to bubble trap 120. The cartridge 200 is consumable portion of the blood circuit that includes portions of the blood circuit that contact the patient's blood. The return draw flow control mechanism 216, pump 210, and draw flow control mechanism 212 are shown in dashed lines because these are a part of the console system and are reusable. Similarly, the return pressure sensor 238 and/or the draw pressure sensor 240 are reusable; however, in certain embodiments, the return pressure sensor 238 and/or the draw pressure sensor 240 may be part of the single use consumable cartridge and tubing. In some implementations, one or more objects described herein in relation to FIG. 2 may be optional (including, but not limited to bubble trap 208, clamp 212, vent 234, solenoid 236, or transducer 240, and so forth). For example, objects that are represented by dashed lines may be optionally included in the cartridge 200.

The cartridge 200 is configured to interface with components of the console 102 of the delivery system 100 during operation, priming and treatment. A portion of the tubing of the cartridge 200, which can be called a pump tube, is configured to be placed in the pump 210 of the console. The draw line 214 tubing and the return line 218 tubing are oriented to be placed inside the draw flow control mechanism 212 and the return flow control mechanism 216, respectively. The flow control mechanisms 212, 216 are coupled to the console 102. When the cartridge 200 is installed, the flow control mechanisms 212, 216 align with the draw and return lines 214, 218 to enable the flow control mechanisms to restrict fluid flow (e.g., by clamping) in the draw and return lines 214, 218. The draw flow control mechanism 212 and the return flow control mechanism 216 are actuated by control signals of a controller of the console 102. Similarly, the pump 210 is coupled to the console 102. The pump 210 is activated by control signals of the controller of the console for pumping in either the draw line direction or the return line direction as needed.

The piston device 202 includes a mechanical device for drawing saline from the fluid source. The fluid from the IV source is drawn through tubing into a piston chamber. The piston moves vertically in the chamber based on signals from a piston actuator. A load cell determines the force required to move the piston. A stepper motor controls the motion of the actuator. An encoder reports the piston position based on the stepper motor rotor location. A piston top sensor and piston bottom sensor can detect when the piston moves to an edge of the chamber. The position of the piston determines how much fluid from the saline bag is sent to the oxygenator.

The piston device 202 is configured to draw saline into the oxygenator 204. The oxygenator 204 is configured to add oxygen to the saline from the saline bag 106. An oxygen pressure line 220 adds oxygen to the oxygenator 204. The oxygenator 204 is coupled to an oxygen vent 226 and an oxygen vent solenoid 228 that controls operation of the vent 226. The oxygenator vent 226 is configured to vent excess air from the oxygenator if the oxygen pressure exceeds a threshold value.

The oxygenator 204 includes an oxygen chamber, an atomizer, and a valve manifold. The valve manifold includes several valves such as a fill valve, a flush valve, and a supersaturated oxygen $SSO_2$ flow valve (not shown). Each of the fill valve, flush valve, and $SSO_2$ flow valve are controlled by a respective solenoid. A fill solenoid opens/closes the fill valve. A flush solenoid opens/closes the flush valve 406. A $SSO_2$ flow solenoid opens/closes the flow valve. An $SSO_2$ level sensor 400 indicates a level of the gas-enriched liquid in the oxygenator.

The oxygen chamber is connected to the oxygen pressure line and the oxygen vent. The oxygenator releases excess oxygen through oxygen vent 426 and receives additional oxygen through oxygen pressure line. The oxygenator receives fluid from the piston chamber. The atomizer includes a central passageway in which a one-way valve is disposed. When the fluid pressure overcomes the force of the spring in the one-way valve and overcomes the pressure of the oxygen within the atomizer chamber, the fluid travels through the passageway and is expelled from a nozzle at the end of the atomizer.

The nozzle forms fluid droplets into which the oxygen within the atomization chamber diffuses as the droplets travel within the atomization chamber. This oxygen-enriched fluid is referred to a $SSO_2$ solution. The nozzle is preferably a simplex-type, swirled pressurized atomizer nozzle including a fluid orifice of about 0.004 inches diameter to 0.005 inches diameter. The droplets infused with the oxygen fall into a pool at the bottom of the atomizer chamber. Since the atomizer will not atomize properly if the level of the pool rises above the level of the nozzle, the level of the pool is controlled to ensure that the atomizer continues to function properly. Once the oxygen has been dissolved into the saline using the controlled pressure, the gas-enriched saline is sent to the blood mixing chamber 206 for mixing with blood in the blood circuit.

The blood mixing chamber 206 is connected to the oxygenator 204. The blood mixing chamber 206 is thus a part of the blood circuit. The blood mixing chamber 206 is positioned between the pump 210 tubing and the return line flow control mechanism 216 and bubble detector 126. A blood mixing chamber 230 is configured to vent any room air and/or air bubbles from the blood mixing chamber 230. A blood mixing chamber vent solenoid 232 controls operation of the vent 230.

The blood mixing chamber 206 includes a volume configured to receive gas-enriched saline from the oxygenator 204. The blood mixing chamber includes low sensor and a high sensor. The low sensor is configured to detect when the blood mixing volume 502 is empty. The high sensor detects when the blood mixing volume is full.

The blood mixing volume vents room air and/or air bubbles from the blood circuit through the vent through the line. The blood mixing chamber receives gas-enriched saline from the oxygenator. The blood mixing chamber receives blood from the pump 210 from the pump tube during operation of the delivery system 100. The gas-enriched saline from the oxygenator 204 mixes with the blood from the draw line of the blood circuit. A return pressure sensor measures pressure in the blood circuit on the return line side of the pump 210. The blood from the blood circuit passes through the blood mixing volume and mixes with the gas-enriched saline from the oxygenator 204. The return line draws blood out of the blood mixing volume to the bubble detector 126.

The blood mixing chamber 206 oxygenator and piston chamber may be located in a single housing or separate from one another. The pump 210 is configured to interface with a pump tube. The pump tube connects the bubble trap 208 to the pump 210. The pump tube connects the blood mixing chamber 210 to the pump on of the opposite side of the pump 210 from the bubble trap 208. Blood in the blood circuit during operation of the delivery system 100 thus comes from the draw line 214 through the bubble trap, is pumped by the pump 210, goes through the blood mixing chamber 206, and then goes through or passes by the bubble detector 126 in the return line 218.

A bubble trap 208 may be provided and configured to remove room air and/or air bubbles from the blood circuit. The bubble trap 208 has a bubble trap volume configured to receive blood from the draw line. The bubble trap volume vents room air and/or air bubbles from the volume to the bubble trap vent. Bubbles rise to the top of the volume and are vented. The bubble trap volume has a low sensor to detect when the bubble trap volume is empty. The bubble trap volume has a high sensor to detect when the bubble trap volume is full. When the volume is full of blood, the bubble trap 208 is primed.

Figure 3:
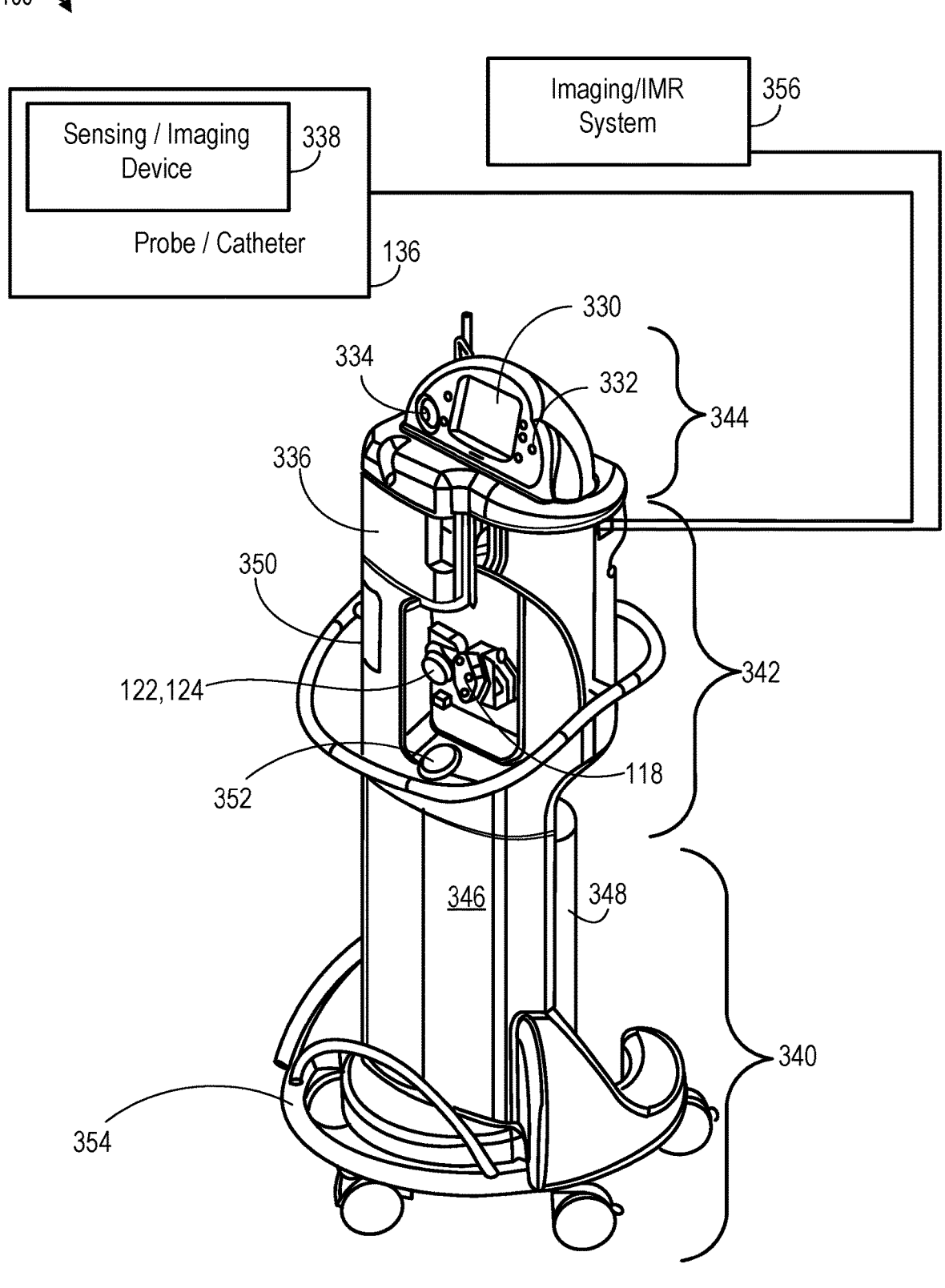
FIG. 3 shows a perspective view of the system of FIGS. 1A, 1B, and 2.

FIG. 3 shows the system 100 of FIG. 1A for administering gas-enrichment therapy e.g., SSO2 therapy in greater detail. The system 100 for administering SSO2 therapy generally includes three component devices: the main control system, the gas enrichment system (e.g., oxygenation cartridge), and the infusion device (e.g., an infusion catheter). These devices function together to create a highly oxygen-enriched saline solution called $SSO_2$ solution. Blood is mixed with the $SSO_2$ solution producing supersaturated oxygen-enriched blood. The supersaturated oxygen-enriched blood is delivered to the patient. The system 100 may have a modular design comprising three removable modules such as a base module 340, the mid-section control module 342, and the display module 346. The system 100 also has a sensing catheter or probe of the image or sensor system 338, which can be implemented via a catheter (e.g., catheter 136) in accordance with certain implementations. A gas tank receptacle 346 is provided on the backside of the base module 340 for receiving and housing a standard "E-bottle" USP oxygen tank 348. The oxygen tank 348 is mounted to the system via a gas tank adapter. A suitable gas, such as oxygen, is delivered from the oxygen tank 348, to a second chamber within an oxygenation cartridge. The physiologic liquid, e.g., saline, from a first chamber is pumped into the second chamber and atomized to create a supersaturated oxygen-enriched physiologic solution. This supersaturated oxygen-enriched physiologic solution is then delivered into a third chamber of the oxygenation cartridge along with the blood from the patient. As the patient's blood mixes with the supersaturated oxygen-enriched physiologic solution, supersaturated oxygen-enriched blood is created and then delivered to a targeted major epicardial artery, e.g., the left main coronary artery, via an infusion catheter.

An imaging system or IMR system 356 can be included to provide imaging or IMR data to the system 100, independent from the probe or catheter 136 that is gathering data from the vasculature of the patient. For example, an angiogram imaging system 356 can be used in addition to a catheter or probe 136 for gathering the imaging data and estimating the IMR of the patient. The imaging or IMR system 356 can send the estimated IMR value or imaging data to the controller 102 for controlling delivery of gas-enriched liquid to the patient. The imaging or IMR system 356 can use a separate port from the catheter or probe 136 (as shown in FIG. 3) for communicating with the controller 102 of the system 100. In some implementations, the imaging or IMR system 356 can use a same port as the catheter or probe 136 for communicating with the controller 102 of the system 100. In some implementations, the imaging or IMR system 356 is included as part of the delivery system console. In some implementations, the imaging or IMR system 356 may communicate wirelessly with the controller 102.

Each of the three modules 340, 342, 344 of the system 100 may include doors or access panels for protecting and accessing the various components housed therein. For example, the mid-section control module 342 includes a hinged door 336 for enclosing the gas-enrichment system (i.e. the cartridge) and access panel 350 for covering the access window to the internal space of the module. A safety switch (e.g. an emergency stop switch 352) may be provided so that a user can initiate a shutdown of the system in the same fashion even if the system is operating within its prescribed bounds.

In the above particular embodiment, the body of the base module 340 is made up of a tubular chassis situated on a circular-shaped pedestal 354. A plurality of wheels are mounted on the bottom of the circular-shaped pedestal to provide mobility for the system. The wheels have a locking mechanism for keeping the wheels stationary. The base chassis houses certain electrical and mechanical components including a battery (not shown), a power supply (not shown), and connectors for connecting the base module 340 to the mid-section main module 342. The user interface 134 includes a screen 330, buttons 332, knobs 334, and other controls for interaction with the delivery system 100.

Figure 4:
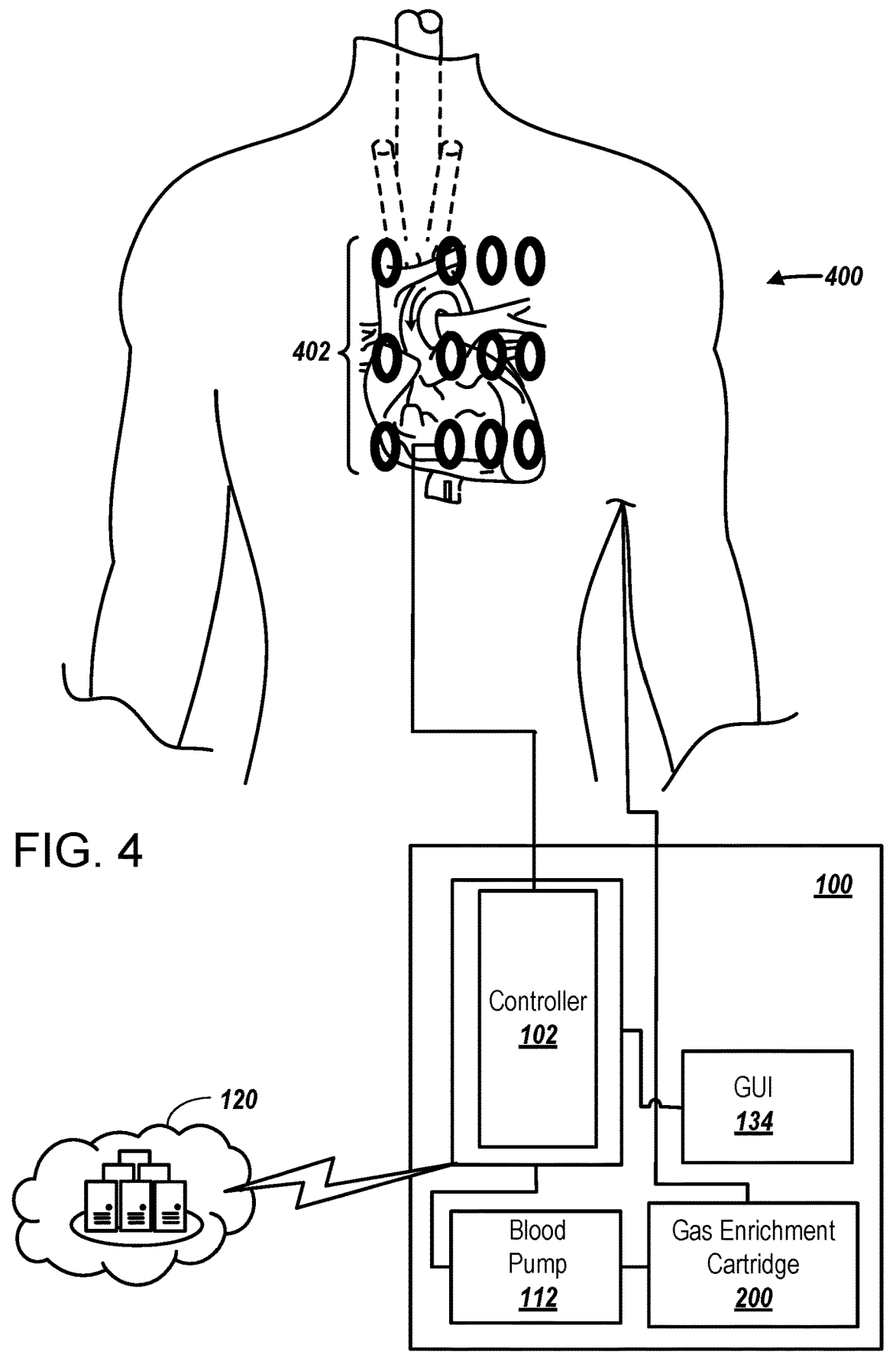
FIG. 4 shows a schematic of a system with impedance tomography sensors for use with the system of FIG. 1A to FIG. 3.

In another example, a delivery system 400, as shown in FIG. 4, including system 100, may perform a process for controlling the delivery of oxygen-enriched blood to a patient based on feedback from one or more sensors or electrodes 402 used to estimate microvascular resistance in the vasculature of the patient.

The delivery system 400 is configured to generate a tomographic map of measured impedance values generated by an impedance tomography sensor system 402. Electrical impedance tomography (EIT) is a noninvasive type of medical imaging in which the electrical conductivity, permittivity, and impedance of a part of the body is inferred from surface electrode measurements and used to form a tomographic image of that tissue region. The delivery system 400 causes delivery of gas-enriched blood generated by a gas enrichment system to a patient to provide supersaturated gas e.g., oxygen, therapy to the patient. The delivery system 400 causes an electrical current to be applied to a tissue of the patient between a plurality of sensors in the form of external electrodes positioned on the external surface of the patient's body (e.g., on the patient's chest and back). The external electrodes may be coupled to the controller via one or more cables or other wired connections. The controller 104 of the system 400 receives a plurality of signals from the electrodes 402 that correspond to measured impedance values from the tissue among the plurality of external electrodes. The controller 102 generates an impedance tomographic map based at least in part of the measured impedance values. Based at least in part on the impedance distribution of the impedance tomographic map, the microvascular resistance of a region of the vasculature of the patient is estimated. In certain implementations, estimating the microvascular resistance may be based at least in part on an average impedance of the impedance distribution. In other implementations, estimating the microvascular resistance may be based at least in part on a product of local impedance and volume of the impedance distribution. Microvascular resistance may be estimated in various regions of the vasculature, including, e.g., in a cardiac region or muscular region.

In certain implementations, a catheter (not shown) may be used where the delivery system 400 causes an electrical current to be applied to a tissue of the patient between electrodes positioned on a catheter located in the vasculature, e.g., the left main (LM) coronary artery, and a plurality of external electrodes positioned on the external surface of the patient's body. Signals from the electrodes 402 correspond to measured impedance values from the tissue between the catheter electrode and the plurality of external electrodes.

The controller 102 may be used to generate a map of measured impedance values in a tissue area having an infarct and to compare the tomographic map of measured impedance values in that tissue area to a baseline tomographic map of measured impedance values in the tissue area to estimate changes in microvascular resistance or blood perfusion and/or changes in infarct size in the patient throughout SSO2 therapy. The mapped areas and any changes in microvascular resistance or blood perfusion and/or changes in infarct size may be stored by the controller 102 in a memory device 382 and may be tagged for future reference. The controller 102 correlates mapped zones with low impedance values to tissue zones with decreased microvascular resistance or increased blood perfusion and/or reduced infarct size. For ischemic tissue, a higher impedance and greater microvascular resistance would be expected because there would be less blood present in the ischemic tissue compared to non-ischemic tissue or tissue with increased blood perfusion and reduced microvascular resistance. The controller 102 may also overlay and spatially align these mapped zones on other mapped images of the same area or the same infarct zone, such as MRI or CT images.

The delivery of oxygen-enriched blood to the patient may be controlled based on the tomographic map of measured impedance values and estimated microvascular resistance. For example, the location of the delivery catheter can be adjusted and/or the rate of delivery of the oxygen-enriched blood (i.e. as controlled by a blood pump of the system) can be adjusted. In certain embodiments, if the tomographic map has regions not showing a decrease in impedance of less than a predetermined threshold, e.g. 10%, or if the estimated infarct size based on the tomographic map has not been reduced by more than some other predetermined threshold, e.g. 15%, the SO2 in the blood can be increased based on the tomographic map of measured impedance values and/or the deduced changes in infarct size. The SO2 in the blood can be decreased or stopped based on exceeding a threshold in either the impedance of a region of the tomographic map or the estimated infarct size. The tomographic data are used by the controller 102 to estimate the microvascular resistance in the mapped vasculature region and for titrating or controlling the $SSO_2$ delivery based on the tomographic data and estimated microvascular resistance.

The electrodes may be any type of electrode suitable for external use on the body of the subject, such as wet or dry self-adhesive medical electrodes typically used to measure electrical signals on the body of a subject. The Sheffield Mark 3.5 and the Enlight 1800 are exemplary electric impedance tomography technologies that may be implemented to provide imaging feedback useful for controlling the SSO2 therapy delivered by the system 400.

The system 400 is configured to have the plurality of electrodes 402 for placement on an exterior of the patient. The controller 102 measures the impedance values from a tissue area between one or more pairs of the plurality of electrodes, generates a tomographic map based on the measured impedance values, estimates a blood perfusion in the tissue area based on the tomographic map, and estimates, based on the blood perfusion, a change in the value of the one or more physiological parameters indicative of the microvascular resistance of the vasculature of the patient.

FIG. 5 shows a flow diagram of a process 500 for controlling $SSO_2$ delivery by one or more of the systems described herein, such as in relation to FIG. 1A-FIG. 4. In some implementations, the process 500 is performed by the controller (e.g., controller 102) of the delivery system 100. The process 500 for controlling gas-enrichment therapy in a patient includes providing (502) a gas-enrichment system configured to enrich a liquid with gas to form a gas-enriched liquid and to mix the gas-enriched liquid with blood to form a gas-enriched blood. The process 500 includes delivering (504) the gas-enriched blood to the patient. The process 500 includes receiving (506), at a controller coupled to a sensor configured to measure one or more physiological parameters indicative of a microvascular resistance of a vasculature of the patient, one or more signals from the sensor corresponding to a measured value of the one or more physiological parameters. The process 500 includes estimating (508), based on the measured value, the microvascular resistance in the vasculature of the patient. The process 500 includes generating (510), based on the microvascular resistance in the vasculature of the patient, an alert or control signal for titrating or controlling an amount of the gas-enriched blood delivered to the patient.

In some implementations, the control signal is configured to control a pump configured to pump the gas-enriched blood for delivery into the patient. The process 500 includes causing the pump to pump blood to and from the gas-enrichment system and the patient based on sending the control signal to the pump. The sensor can include a flow sensor. The one or more physiological parameters include a flow rate of blood in the vasculature of the patient. In some implementations, the sensors include a pressure sensor. The one or more physiological parameters include a pressure of blood in the vasculature of the patient.

In some implementations, the process 500 includes sending, by the controller, the control signal to a pump configured to pump the gas-enriched blood for delivery into the patient. The process 500 includes causing, based on sending the control signal, the pump to increase a pump speed or reduce a pump speed to increase or reduce the amount of the gas-enriched blood delivered to the patient.

In some implementations, reducing the amount of the gas-enriched blood delivered to the patient includes determining that a change in the value of the one or more physiological parameters represents a reduced microvascular resistance in the vasculature of the patient. The process 500 includes, in response to determining that the change in the value represents the reduced microvascular resistance, generating the control signal that is configured to cause a reduction in the amount of the gas-enriched blood delivered to the patient.

In some implementations, increasing the amount of the gas-enriched blood delivered to the patient includes determining that a change in the value of the one or more physiological parameters represents an increased microvascular resistance in the vasculature of the patient. The process 500 includes, in response to determining that the change in the value represents the increased microvascular resistance, generating a control signal that is configured to cause an increase in the amount of the gas-enriched blood delivered to the patient.

In some implementations, the sensors include each of a flow sensor and a pressure sensor, and the physiological parameters comprise a flow rate of the blood in the vasculature of the patient and a blood pressure in the vasculature of the patient. The process 500 includes estimating a microvascular resistance in the patient based on a ratio of the flow rate and the blood pressure generating the control signal or an alert based on the estimated microvascular resistance.

In some implementations, generating the control signal or alert is performed in real-time or near-real time during delivery of the gas-enriched blood to the patient. The delivery of the gas-enriched blood to the patient is not paused during measurement of the one or more physiological parameters. The measurement of the one or more physiological parameters represents a contemporaneous status of the patient for the delivery of the gas-enriched blood to the patient.

In some implementations, receiving one or more signals corresponding to a measured value of the one or more physiological parameters from the sensor includes receiving a series of measured values of the one or more physiological parameters from the sensor. The series of measured values can correspond to a period of time during delivery of the gas-enriched blood to the patient. The process 500 includes determining, based on the series of measured values corresponding to the period of time, whether the value of the one or more physiological parameters is increasing or decreasing over time. The process 500 includes generating, based on determining that the value of the one or more physiological parameters is increasing or decreasing over time, the control signal or alert for increasing or reducing the amount of the gas-enriched blood delivered to the patient.

In some implementations, the process 500 includes receiving angiogram data representing the patient for a time period contemporaneous with or after the delivery of the gas-enriched blood to the patient and calculating or estimating an IMR based on the angiogram data. The process 500 includes generating, based on the angiogram data, the control signal configured to increase or reduce the amount of the gas-enriched blood delivered to the patient.

In some implementations, the process 500 includes receiving, by the controller, pressure data from a pressure sensor coupled to a wire supported at a distal end of a catheter in the vasculature of the patient. The process 500 includes determining, by the controller based on receiving the pressure data, an Index of Microcirculatory Resistance (IMR) value in the vasculature of the patient. The process 500 includes generating, by the controller based on the IMR value, and alert or a control signal configured to increase or reduce the amount of the gas-enriched blood delivered to the patient.

In some implementations, the process 500 includes measuring, by the controller, impedance values from a tissue area between one or more pairs of a plurality of external electrodes configured for placement on an exterior of the patient. The process 500 includes generating, by the controller, a tomographic map based on the measured impedance values. The process 500 includes estimating, by the controller, a blood perfusion in the tissue area based on the tomographic map. The process 500 includes estimating, by the controller based on the blood perfusion, a change in the value of the one or more physiological parameters indicative of the microvascular resistance of the vasculature of the patient.

The entire disclosures of U.S. Pat. Nos. 6,743,196, 6,582,387, 7,820,102 and 8,246,564 are expressly incorporated herein by reference.

Figure 6:
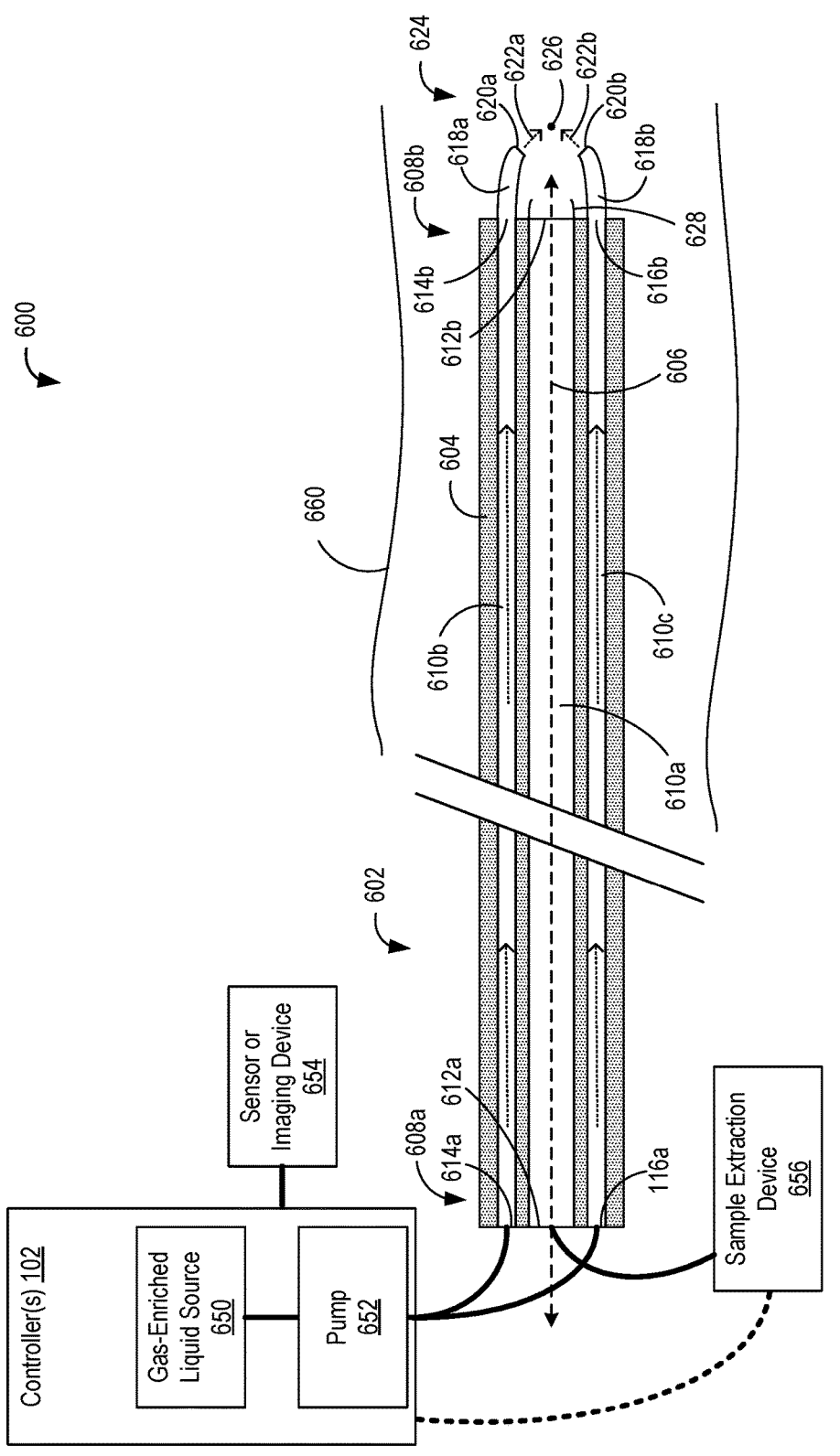
FIG. 6 is a diagram of an example gas-enrichment system for delivering gas-enriched liquid within the vasculature of a patient.

FIG. 6 shows an example system 600 for enriching a bodily liquid with a dissolved gas or gas enriched liquid inside of an enclosed area of a body. As an example, the system 600 can be used to enrich a patient's blood with supersaturated oxygen-enriched liquid or supersaturated liquid within the vasculature of the patient thereby delivering supersaturated oxygen (SSO$_2$) therapy to a patient, increasing oxygen in the blood and diffusion of oxygen into tissue. In certain implementations, oxygen-enriched liquid or solution, e.g., supersaturated oxygen-enriched liquid or solution, may include liquid having a dissolved O$_2$ concentration of 0.1 ml O2/ml liquid (STP) or greater or 0.1-6 ml O2/ml liquid (STP) or 0.2-3 ml O2/ml liquid (STP) (e.g., without clinically significant gas emboli).

As shown in FIG. 6, the system 600 includes a catheter 602, a gas enriched liquid source 650, a pump 652, a sensor 654, and a sample extraction device 656. The catheter 602 is configured to be inserted into the vasculature of a patient, to facilitate the delivery of a gas enriched liquid (e.g., from the gas enriched liquid source 650) into the vasculature of the patient via the pump 652. Further, the catheter 602 is configured to facilitate the measurement of one or more properties of the patient's blood within the patient's vasculature (e.g., by providing the sensor 654 access to the patient's vasculature) and/or to facilitate the collection of blood samples from the patient's vasculature (e.g., by providing the sample extraction device 656 access to the patient's vasculature). For example, the sensor 654 may positioned on the distal (or first) end 608a of the catheter 602 or in a communicating lumen of the catheter 602. The sensor 654 can detect various blood parameters (e.g., partial pressure of oxygen in the patient's blood (pO$_2$), the oxygen saturation of the patient's blood (SO$_2$), the flow rate of the patient's blood, a temperature of the patient's blood), during treatment or after treatment is paused or completed. In some implementations, the sensor or imaging device 654 is part of the catheter. In some implementations, the sensor or imaging device 654 is part of the system including the controller 102 or separate from the controller but in communication with the controller.

The catheter 602 includes an elongated catheter body 604 (e.g., extending along a longitudinal axis 606 through the center of the catheter body 604) having a proximal (or second) end 608b opposing the distal end 608a. In some implementations, the catheter can have a circular, elliptical, or ovular cross-section along a portion of or an entirety of its length. In some implementations, the catheter body 604 can be flexible (e.g., such that it can be bent or curved at one or more locations along its length. In some implementations, at least a portion of the catheter 602 and/or the catheter body 604 can be composed of polycarbonate, glass, ceramic, stainless steel, polyether ether ketone (PEEK), polyether block amide (PEBA) (e.g., PEBAX produced by Akrema S.A., Colombes, France), acrylonitrile butadiene styrene (ABS), polyimide, and/or other suitable materials. In some implementations, the catheter body 604 can have an outer diameter ranging from 4 F to 12 F, or for example, 4 F to 6 F (according to the French scale—about 1.33 mm to 4 mm or about 1.33 mm to 2 mm).

Further, the catheter 602 includes multiple lumens extending through the catheter body 604. In this example, the catheter 602 includes one or more communicating lumens 610a extending through a center of the catheter body 604 (e.g., along the longitudinal axis 606). At least two additional lumens 610b and 610c may extend through opposing sides of the catheter body 604 (e.g., parallel to the communicating lumen 610a). Each of the lumens 610a-610c can have a circular, elliptical, or ovular cross-section along a portion of or an entirety of its length. In some implementations, the communicating lumen 610a can have an inner diameter ranging from 0.020 inches to 0.045 inches (about 0.5 mm to about 1.1 mm).

Each of the lumens 610a-610c includes a respective input aperture and a respective output aperture. For example, the communicating lumen 610a includes an input aperture 612a on the first (or distal) end 608a of the catheter body 604 and an output aperture 612b on the second (or proximal) end 608b of the catheter body 604. As another example, the lumen 610b includes an input aperture 614a on the first end 608a of the catheter body 604 and an output aperture 614b on the second end 608b of the catheter body 604. As another example, the lumen 610c includes an input aperture 616a on the first end 608a of the catheter body 604 and an output aperture 616b on the second end 608b of the catheter body 604.

Further, the catheter 602 includes a capillary 618a extending from and in fluid communication with the output aperture 614b of the lumen 610b (e.g., such that fluid can flow from the lumen 610b into the capillary 618a. The capillary 618a terminates at an output aperture 620a. In some implementations, the capillary 618a can have an inner diameter between 40 microns and 100 microns. In some implementations, the capillary 618a can have an outer diameter between 140 microns and 160 microns. In some implementations, the capillary 618a can have a length ranging from 5 cm to 10 cm or be a length "l" which is substantially equal to the diameter of the catheter tip or distal end.

The catheter 602 also includes a capillary 618b extending from and in fluid communication with the output aperture 616b of the lumen 610c (e.g., such that fluid can flow from the lumen 610c into the capillary 618b. The capillary 618b terminates at an output aperture 620b. In some implementations, the capillary 618b can have an inner diameter from 40 microns to 100 microns. In some implementations, the capillary 618b can have an outer diameter from 140 microns to 400 microns. In some implementations, the capillary 618b can have a length ranging from 5 cm to 10 cm or be a length "l" which is substantially equal to the diameter of the catheter tip or distal end.

In some implementations, the capillaries 618a and 618b may have identical or different sized inner and/or outer diameters. In some implementations, the capillaries 618a and 618b may have identical or different sized lengths.

During an example usage of the system 600, the gas enriched liquid source 650 and the pump 652 are coupled to the catheter 602, such that the gas enriched liquid source 650 and the pump 652 are in fluid communication with the input apertures 614a and 616a of the lumens 610b and 610c, respectively. As an example, one or more fluid-tight tubes can be used to convey gas enriched liquid from the gas enriched liquid source 650 to the pump 652, and from the pump 652 to the input apertures 614a and 616b. In some implementations, one or more fluid-tight tubes can be used to convey gas enriched liquid from the gas enriched liquid source 650 to the input apertures 614a and 616b, where at least a portion of the one or more fluid-tight tubes are coupled to a peristaltic pump or form part of the peristaltic pump, which urges fluid from the gas enriched liquid source to the input apertures 614a and 616b. In some implementations, the tubes can be secured to the input apertures 614a and 616b using a fitting or connector, such as a high-pressure Luer fitting.

In some implementations, the gas enriched liquid source 650 can include one or more storage tanks for storing the gas enriched liquid. In some implementations, the gas enriched liquid can be a supersaturated oxygen-enriched liquid or supersaturated liquid, such as a liquid having a dissolved oxygen ($O_2$) concentration between 0.2 and 3 ml $O_2$/ml solvent (which is the concentration equivalent of 100 psi to 1500 psi). In some implementations, the gas enriched liquid can include liquid enriched with oxygen, ozone, inert gas, nitrogen, nitrous oxide, carbon dioxide, and/or air. In some implementations, the gas enriched liquid source 650 may include an oxygenation device, which is operated by a console or hardware component that controls operation of the oxygenation device, as described in U.S. Pat. No.

9,919,276, the entire disclosure of such patent being expressly incorporated herein by reference in its entirety. The console or hardware component may include a controller, processor, memory and associated circuitry. The oxygenation device may include a fluid supply chamber for receiving a physiologic liquid e.g., saline from an IV bag, and an atomization chamber for receiving a suitable gas, e.g., oxygen from an oxygen tank. The saline is pumped into the oxygen-pressurized atomization chamber and atomized to create gas-enriched or supersaturated liquid, e.g., supersaturated oxygen-enriched saline or supersaturated saline. In certain implementations, the gas-enriched liquid can be oxygen-enriched liquid or solution, e.g., supersaturated oxygen-enriched liquid or solution, may include liquid having a dissolved $O_2$ concentration of 0.1 ml O2/ml liquid (STP) or greater or 0.1-6 ml O2/ml liquid (STP) or 0.2-3 ml O2/ml liquid (STP) (e.g., without clinically significant gas emboli). In some implementations, the gas enriched liquid can be a supersaturated oxygen-enriched liquid or solution (e.g., saline with a dissolved $O_2$ concentration in saline of 0.1 ml O2/ml saline (STP) or greater or 0.1-6 ml O2/ml saline (STP) or 0.2-3 ml O2/ml saline (STP) (e.g., without clinically significant gas emboli).

Further, a portion of the catheter 602 is inserted into a patient, such as the second end 608b of the catheter body 604 is positioned within a vasculature of a patient (e.g., a blood vessel 660, such as a vein or artery). After the catheter 602 has been inserted into the patient, the pump 652 is activated, such that it draws the gas enriched liquid from the gas enriched liquid source 650, and pumps the gas enriched liquid, e.g., supersaturated liquid, into each of the lumens 610b and 610c. The gas enriched liquid flows through the lumens 610b and 610c and into the capillaries 618a and 618b and is expelled from the output apertures 620a and 620b as two respective streams 622a and 622b.

In some implementations, the system 600 can be configured to expel streams according to different flow rates and/or pressures. For example, the system 600 can be configured to expel streams between 1 mL/minute (e.g., at a pressure of 100 psi, about 690 kPa) to 3 mL/minute (e.g., at a pressure of 300 psi, about 2 MPa).

The capillaries 618a and 618b are configured such that the streams 622a and 622b intersect with one another and mix in a mixing region 624 within the vasculature of the patient. For example, the capillaries 618a and 618b can define respective paths that are angled relative to the longitudinal axis 606, such that the streams 622a and 622b are expelled from the output apertures 620a and 620b at respective angles relative to the longitudinal axis 606. In some implementations, the capillaries 620a and 620b can be configured such that the streams 622a and 622b intersect at a point 626 beyond the tip of the catheter 602 (e.g., where the point 626 is on or around the longitudinal axis 606). For example, the streams 622a and 622b may mix without bubble formation or without significant bubble formation in the mixing region 624 at a distance downstream from the output apertures of the capillaries 618a and 618b.

Further, the communicating lumen 610a provides access to the vasculature of the patient. For example, in some implementations, a sensor 654 can be at least partially inserted into the communicating lumen 610a, such that it is in fluid communication with the blood of the patient. In other implementations, the sensor may be located outside of the communicating lumen or on a catheter wall. The sensor 654 can obtain one or more sensor measurements regarding the blood and provide feedback regarding measured parameters affected by the $SSO_2$ therapy in order to optimize the $SSO_2$ therapy. For example, the sensor 654 can measure a partial pressure of oxygen of the patient's blood, an oxygen concentration or $SO_2$ of the patient's blood, a pressure of the patient's blood, e.g., arterial blood pressure, a flow rate of the of the patient's blood, and/or a temperature of the of the patient's blood.

Examples of such sensors include the following.

One example of a sensor for measuring a partial pressure ($pO_2$) of oxygen or oxygen saturation $SO_2$ in the patient's blood is a pulse oximeter. A pulse oximeter may be used for estimating arterial $pO_2$ or $SO_2$. Pulse oximetry estimates the percentage of oxygen bound to hemoglobin in the blood. A pulse oximeter uses light-emitting diodes and a light-sensitive sensor to measure the absorption of red and infrared light. In another example, a sensor for measuring partial pressure of oxygen comprises an electrode such as a Clark electrode for measuring $pO_2$. A Clark electrode is an electrode that measures ambient oxygen concentration in a liquid using a catalytic platinum surface according to the net reaction $O2+4 e-+4H+\rightarrow2H_2O$. The various sensors may be coupled to a controller of the system via a cable or other wired connection or via a wireless connection.

The processor can receive the signals from these sensors, which signals correspond to the measured values of $pO_2$. The processor compares the measured $pO_2$ to a target range of blood $pO_2$, e.g., 760-1500 mmHg (about 100 kPa to 200 kPa). The target range may be calculated based on a blood flow rate of 50-150 ml/min, saline flow rate of 2-5 ml/min and dissolved $O_2$ concentration in saline of 0.2-3 ml $O_2$/ml saline (STP). The controller can adjust the saline flow rate and/or dissolved $O_2$ concentration in saline based on the measured $pO_2$ in blood to achieve an arterial blood $pO_2$ within the target range. The processor may generate an alert, e.g., through a user interface, audible alarm and/or visual alarm that indicates the level of $pO_2$. The measured $pO_2$ indicates the effectiveness of the supersaturated oxygen therapy, letting the caregiver know if the $pO_2$ in blood is within the target range for optimizing the delivery of oxygen to the patient's ischemic tissue. In certain implementations, the processor may control the delivery of supersaturated oxygen therapy by modifying one or more of the above referenced saline or oxygen parameters based on the signals received from the sensors.

Another example of a sensor is an $O_2$ fluorescence probe. The fluorescence probe may be coupled to a controller of the system via a cable or other wired or wireless connection. A light source of the $O_2$ fluorescence probe is illuminated. A fiber optic cable can be used to provide light to the light source in certain implementations, where the fiber optic cable is connected to the controller of the system. The fluorescence of a sensor molecule of the $O_2$ fluorescence probe is measured. The sensor molecule can include fluorophore. A signal is received by the processor from the $O_2$ fluorescence probe based on the fluorescence measurement. Fluorescence is measured by measuring the lifetime or decay of the fluorescence intensity signal from the illuminated sensor molecule (e.g., fluorophore) on the fluorescence probe. The decay of this signal is caused by the quenching effect of oxygen molecules in the blood or in tissue on the fluorescence intensity signal of the sensor molecule. The processor can determine the oxygen concentration, $SO_2$ or $pO_2$ in blood or tissue based on the quenching effect of oxygen on the florescence intensity signal of the florescence probe. Changes in the amount of time that is required for the signal to decay due to oxygen quenching are indicative of the local oxygen concentration, $SO_2$ or $pO_2$ in blood or tissue. The processor generates an alert, e.g., through a user interface, audible alarm and/or visual alarm, based on the determined oxygen concentration, $SO_2$ or $pO_2$ in blood or tissue. The alert may indicate the effectiveness of the supersaturated oxygen therapy. The determined oxygen concentration, $SO_2$ or $pO_2$ indicates the effectiveness of the supersaturated oxygen therapy, letting the caregiver know if the oxygen concentration, $SO_2$ or $pO_2$ in blood is within a predefined target range (e.g., the expected range for a healthy individual) for optimizing the delivery of oxygen to the patient. In certain implementations, the processor may control the delivery of supersaturated oxygen therapy by modifying one or more of the saline or oxygen parameters, e.g., saline flow rate or dissolved O2 concentration in saline, based on the determined oxygen concentration, $SO_2$ or $pO_2$ values.

Another example of a sensor is a temperature sensor located on or in the catheter. For example, a thermistor may be utilized to measure the blood temperature of the patient. The processor can receive signals from the thermistor, which signals correspond to the measured values of the blood temperature. The processor may generate an alert, e.g., through a user interface, audible alarm and/or visual alarm that indicates the blood temperature, which may alert the caregiver of a hypothermic or hyperthermic, e.g., febrile, state of the patient.

An example sensor for measuring an arterial pressure of the patient's blood would be a pressure sensor positioned in or coupled to the communicating lumen. The communicating lumen may be used for direct measurement of arterial pressure. The communicating lumen may be connected to a fluid-filled system, which is connected to an electronic pressure transducer. A change in detected blood pressure may be indicative of improved perfusion and/or restored flow in ischemic tissue as a result of the $SSO_2$ therapy. The therapy may result in improved heart function. In certain implementations, the processor may control the delivery of supersaturated oxygen therapy based on the arterial pressure feedback.

An example sensor used to determine a blood flow rate includes a temperature sensor, e.g., a thermistor, thermocouple or thermal anemometer. A temperature sensor may be located on a catheter tip, capillary tip or in the communication lumen. The temperature sensor may be heated, such that the sensor temperature is raised. As blood flows past the temperature sensor, the degree to which the temperature sensor cools down is indicative of the flow rate past the temperature sensor. The determined blood flow rate may be fed back to the system and may be indicative of the efficacy of the $SSO_2$ therapy, which results in improved perfusion and/or restored flow in ischemic tissue. In certain implementations, the processor may control the delivery of supersaturated oxygen therapy based on the blood flow rate feedback.

If the sensor is a pressure sensor, the sensor may detect a pressure differential between ambient pressure and arterial pressure or an absolute value of arterial pressure. The pressure sensor may be placed anywhere in the communicating lumen but does not necessarily have to be positioned in the communicating lumen, and can be located outside of the lumen. One example of a pressure sensor is a strain gauge. In a catheter having multiple communicating lumens, a pressure sensor may be located in a first communicating lumen providing an uninterrupted pressure signal while blood sampling may be performed via a second communicating lumen simultaneously. In another example, two pressure sensors can be used, with one located in a first communicating lumen and one located in a second communicating lumen to provide redundancy of pressure readings.

As another example, in some implementations, a sample extraction device 656 can be used to obtain a sample of the patient's blood via the communicating lumen 610a. For example, the sample extraction device 656 can include one or more pumps or syringes to draw a sample of the patient's blood through the lumen 610a and out of the patient's body. The syringe may be coupled to a proximal end of the catheter for sampling. A valve or stopcock may be included at the proximal end of one more lumen of the catheter to control sampling.

In some implementation, the communicating lumen 610a can also be used to guide the catheter 602 within the patient's body. For example, a guide wire can be inserted into the communicating lumen 610a, and manipulated to control the shape and/or position of the catheter 602 within the patient's body. The sample extraction device 656 can, in some examples, be in communication with the controller 102 or controlled by the controller 102. In some implementations, the sample extraction device 656 is a device separate from the controller 102 and can communicate with the controller (e.g., to send data representing the samples or measurements to the controller 102).

Further, the catheter 602 may be configured in such a way that eliminates or otherwise reduces the formation of bubbles within the vasculature of the patient. For example, the streams 622a and 622b mix in a mixing region 624 away from any surfaces of the catheter 602 or capillaries thereby reducing, preventing or reducing the likelihood of bubble formation through nucleation on the surfaces of the catheter 602 or capillaries.

In some implementations, a controller (e.g., controller 102 of FIG. 1A) is connected to the sensor or imaging device 654. The sensor or imaging device 654 can be part of the system 100 including the controller 102. In some implementations, the sensor or imaging device 654 is separate from the controller 102 and can be in communication with the controller. For example, an angiogram imaging device can be controlled by a different controller, and the image data can be sent to controller 102 from the imaging device 654. The sensor or imaging device 654 can include sensors (e.g., 308, 310) of the delivery system 100 of FIG. 1A and/or imaging device (e.g., MRI, angiogram, etc.). The catheter 602 can be included in the delivery system 100 as catheter 136. The controller of the delivery system 100 is configured to estimate a change in the microvascular resistance of the vasculature of the patient, e.g., a regional or local area of the vasculature or microvasculature. In some implementations, titrating or controlling the amount of the gas-enriched liquid delivered to the patient includes determining by the controller 102 that a change in the value of the pressure and/or flow rate from the sensor or imaging device 654 represents a reduced microvascular resistance in the vasculature of the patient. In response to determining that the change in the value represents the reduced microvascular resistance, or the IMR has plateaued, the controller 102 generates a control signal that is configured to cause a reduction in the amount of the gas-enriched liquid delivered to the patient or cause the therapy to stop. In some implementations, titrating or controlling the amount of the gas-enriched liquid delivered to the patient includes determining, by the controller 102, that a change in the value of the flow and/or pressure change represents an increased microvascular resistance in the vasculature of the patient. The controller 102, in response to determining that the change in the value represents the increased microvascular resistance, or that the IMR is increasing, generates a control signal that is configured to cause an increase in the amount of the gas-enriched liquid delivered to the patient. In certain implementations, an alert may be generated to which a caregiver responds by titrating or controlling the therapy appropriately.

In certain implementations, the controller may estimate microvascular resistance by determining the IMR over a period of time and consider the reduction in IMR over that period of time. If the IMR is still decreasing, that may indicate that more gas-enrichment or SSO2 therapy is needed. If IMR has reached a plateau, that may indicate that a maximum benefit of the therapy has been reached, and therapy can be stopped.

In certain implementations, the controller may estimate microvascular resistance by determining the IMR over a period of time and consider the increase in IMR over that period of time. If the IMR is still increasing, that may indicate that more gas-enrichment or SSO2 therapy is needed. If IMR has reached a plateau, that may indicate that a maximum benefit of the therapy has been reached, and therapy can be stopped.

In certain implementations, the system 600 may receive imaging data e.g., angiogram imaging data, representing the vasculature of the patient, and estimate, based on the imaging data and/or measured values of the sensor, a microvascular resistance, e.g., IMR, in the vasculature of the patient to provide feedback for controlling an amount of the gas-enrichment therapy.

Figure 7:
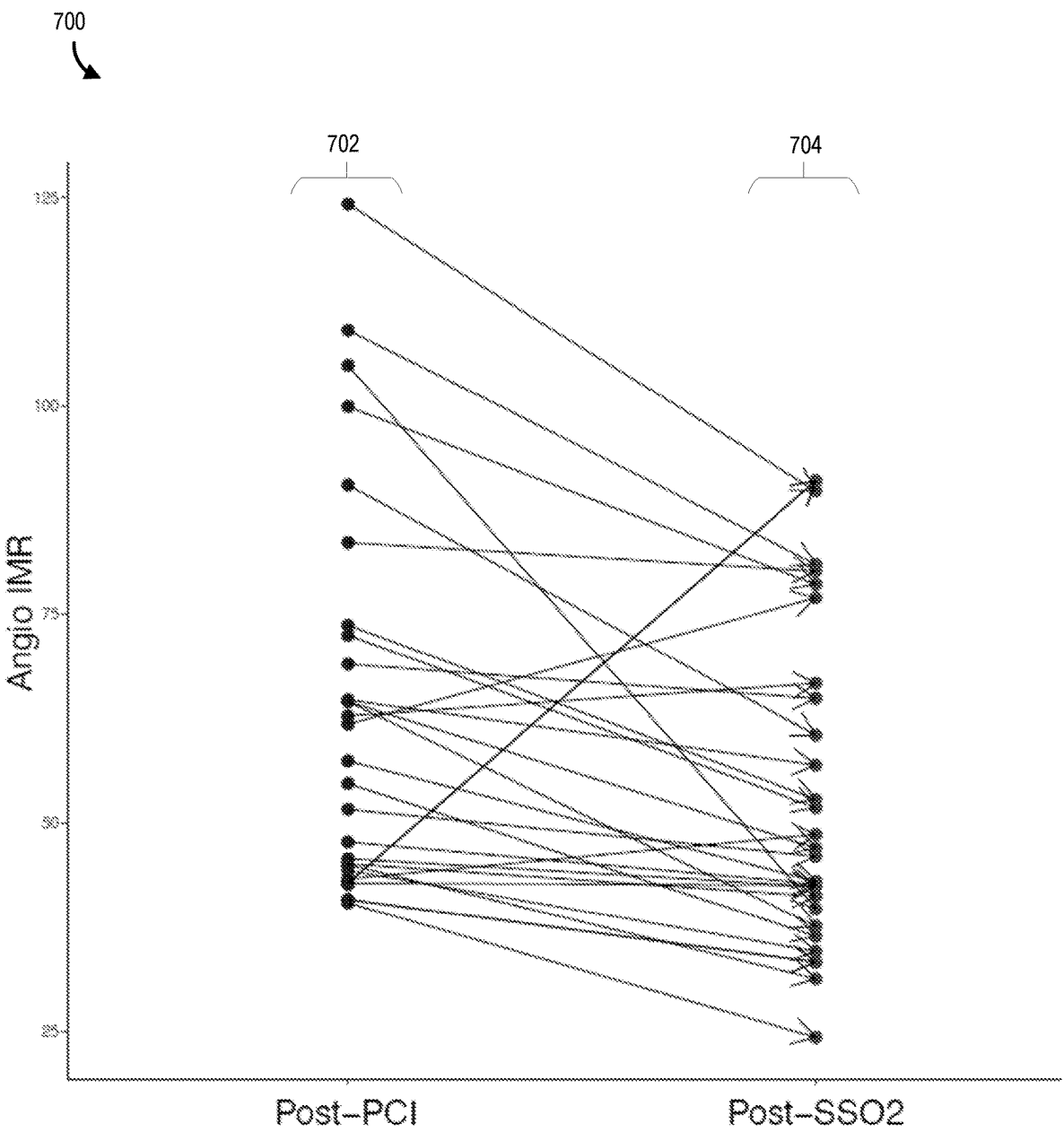
FIG. 7 is a graph including example data.

FIG. 7 is a graph 700 including example values for IMR in patients where the IMR is determined from an angiogram. While this example is described in the context of angiograms, other imaging techniques, such as MRIs, can be used. The graph 700 includes post-PCI IMR values 702 and post SSO2 IMR values 704 (IMR values after PCI followed by SSO2). The post-PCI IMR values occur after percutaneous coronary intervention (PCI) is performed on a patient. PCI refers to procedures for opening clogged coronary arteries for a patient. For example, these procedures can include balloon angioplasty, angioplasty with a stent, rotational atherectomy, and so forth as described herein. The PCI is generally performed with the catheter near the heart, when a contrast dye is injected so that an angiogram can easily represent vessels' narrowed area(s) on an X-ray, as described herein.

IMR is a hemodynamic marker for microvascular dysfunction. IMR provides data for assessment of coronary microvascular status quickly following an interventional procedure. As described previously, IMR can be determined using a wire-based system (wire-IMR). IMR may also be determined by model-based analysis of angiographic films (angio-IMR). In certain implementations, the model-based analysis of angiographic films may be paired with blood pressure data.

The data of graph 700 show a contrast between values 702 for angio-IMR post PCI without $SSO_2$ therapy being performed (e.g., pre-$SSO_2$ infusion and post-PCI) and data values 704 for angio-IMR for post-PCI after $SSO_2$ therapy is performed (e.g., immediately after $SSO_2$ infusion). As shown in graph 700, the angio-IMR values 704 are reduced substantially after $SSO_2$ therapy is performed.

The data values 702, 704 of graph 700 show a significant reduction in median angio-IMR values, by about 9.05, following $SSO_2$ therapy infusion in patients who have post-PCI IMR values over 40. Patients with a post-PCI angio-IMR value over 40 who were treated with $SSO_2$ therapy showed an acute reduction in microvascular resistance. The IMR value of 40 is chosen as a representative threshold in which negative outcomes for post-PCI patient are more likely. Therefore, in populations in which outcomes could be poor, SSO2 therapy was shown to cause a significant improvement to angio-IMR values.

To generate the values 704, an $SSO_2$ therapy system can be used, such as the systems described previously in reference to FIGS. 1A-4. Generally, a PCI is performed. The angiogram is generated after a period of time (e.g., within minutes) of the PCI. The system then performs $SSO_2$ delivery. The SSO2 therapy is paused, and a second angiogram is performed after a period of time (e.g., within minutes) of the therapy. Blood pressure values are collected post-PCI and post-SSO2 delivery. IMR values are determined based on analysis of the angiographic films. For example, angiographic projections are captured, and the controller generates a three-dimensional mesh reconstruction of the coronary arteries and/or vessel path from the inlet of the coronary arterial tree to a most distal position. A mean aortic pressure (MAP) is computed by averaging the pressure waves in successive cardiac cycles. The controller is configured to compute the diastolic flow velocity (e.g., using a thrombolysis in myocardial infarction (TIMI) frame count method or a similar method). A steady-state laminar flow simulation across the stenotic blood vessel in 10-30 is generated.

As described in relation to FIG. 8, the $SSO_2$ therapy can be delivered non-contemporaneously with the gathering of the IMR data, such as through angio-IMR. In other implementations, the SSO2 therapy can be delivered continuously or contemporaneously with the gathering of IMR data (e.g., such as through other forms of imaging). In some implementations, other IMR data gathering techniques can be used that enable continuous and/or simultaneous $SSO_2$ therapy. In some implementations, $SSO_2$ infusion is paused during IMR data gathering and/or IMR determination.

FIG. 8 is a flow diagram of an example process 800 for controlling delivery of gas-enriched blood e.g., oxygen-enriched blood, or gas-enriched liquid, e.g., oxygen-enriched liquid to a patient based on IMR values which are determined from vasculature imaging data. In an example, the process 800 can be used to generate the values 704 of graph 700 described in relation to FIG. 7. The process 800 may be used for controlling oxygen-enrichment therapy delivery to the patient, such as $SSO_2$ therapy delivery, by one or more of the systems described herein, such as in relation to FIG. 1A-FIG. 4.

Processes 500, 800 can be performed by a single system (such as delivery system 100 or any of the systems described in relation to FIGS. 1A-4) or by multiple systems or devices. In some implementations, the process 800 is performed by the controller (e.g., controller 102) of the delivery system 100. For example, a first system or device may generate angiogram images and send them to a second device (e.g., a processor or controller of the delivery system or another system) for calculating the IMR value and performing the gas-enrichment therapy based on the calculated IMR value.

The process 800 for controlling gas-enrichment therapy, e.g., oxygen-enrichment therapy or $SSO_2$ therapy, in a patient includes providing (802) a gas-enrichment system configured to enrich a liquid with gas to form a gas-enriched liquid and to mix the gas-enriched liquid with blood to form a gas-enriched blood. The process 800 includes delivering (804) the gas-enriched blood to the patient. Alternatively, in certain implementations, the gas enriched liquid may be delivered directly to the patient's vasculature, and mix with blood and form gas enriched blood inside the patient's vasculature At step 806, the process includes determining whether gas-enrichment therapy should be paused to gather imaging and IMR data or not paused and operated continuously while imaging and IMR data are generated. In an example, for angio-IMR based data gathering, the gas-enrichment therapy may be paused. For another imaging-based data gathering, the gas-enrichment therapy may not be paused.

The IMR can be calculated based on the angiogram as now described. As previously described, the IMR value represents a blood flow velocity, which can be indicated by a distal pressure. Proximal may be at the beginning of the Left Anterior Descending Artery and distal may about 75 mm down from proximal. In an example, a controller or other processor of the system is configured to generate, from the angiogram data, a three dimensional (3D) model of a coronary vasculature of the patient. The 3D model includes the vasculature up to a threshold length. The threshold length can be about 72 or 75 millimeters. In some implementations, other threshold lengths are possible (e.g., less than 90 mm, 60-90 mm, etc.). The processor or controller of the system processes the blood pressure data including both systolic and diastolic data. The processor or controller can estimate a mean arterial pressure (MAP) based on the processed blood pressure data. The MAP includes a proximal pressure in the coronary vasculature at a length that is equal to 0 (an origin point). The controller or other processor processes the angiogram data to calculate a coronary blood velocity (V) that occurs during diastole. Based on each of the MAP value and the coronary blood velocity value V, the processor or controller is configured to estimate distal pressure. The controller executes a fluid model to perform this computation. The controller or processor, based on the distal pressure and coronary blood velocity value V, determines a value for IMR. The relationship between the distal pressure, V, and the IMR value are based on a constant value K. The controller uses the constant value K (e.g., 2.1) to estimate a hyperemic flow and therefore the IMR values. The controller determines IMR in this manner in a post-PCI scenario, but before $SSO_2$ is performed. This procedure can be repeated by the controller or processor to determine the IMR value for a patient after post-$SSO_2$ is performed using updated angiogram data.

In some implementations, the system determines that gas-enrichment therapy should pause, such as responsive to a determination of what kind of imaging will be used for IMR value estimation. For example, if angio-based IMR is being performed, the system pauses (808) gas-enrichment infusion. As previously stated, the gas-enrichment therapy can pause after a predetermined period of time has passed, such as after 30-60 minutes. A contrast fluid is inserted (810) in order to perform the angiogram. The angiogram image data are captured (812). The angiogram imaging data representing the patient's vasculature is then received 814 at a controller of the gas-enrichment system or other remote system. An IMR in the vasculature of the patient is then estimated based on the angiogram imaging data. The system is configured to generate, based on the IMR in the vasculature of the patient, an alert or control signal for controlling an amount of the gas-enriched blood delivered to the patient. Depending in the patient's IMR values, the system may resume or cease gas-enrichment therapy. In some implementations, the system is configured to resume (820) gas-enrichment therapy once the angiogram imaging data is captured and in parallel with determining the IMR value.

In some implementations, the system determines (806) that the gas-enrichment therapy can continue uninterrupted while still obtaining IMR values. In this example, while gas-enrichment therapy is occurring, the system captures (822) an MRI image or other image of a vasculature of the patient from which an IMR value can be estimated. While gas-enrichment therapy is occurring, MM or other imaging data representing the patient's vasculature is then received at a controller of the gas-enrichment system or other remote system (816) and an IMR in the vasculature of the patient is estimated based on the imaging data. Gas-enrichment therapy can be controlled responsive to determining the IMR value. Specifically, IMR can be determined while the patient is still undergoing gas-enrichment therapy and therapy can be adjusted accordingly. Generally, steps 806, 820, 822, and 824 can be optional, and the delivery system can be configured to automatically pause gas-enrichment therapy for performing imaging and estimating IMR values or determining a blood flow in the vasculature of the patient.

In some implementations, PCI is performed, and an angiogram is taken as representing the baseline IMR value. Gas-enrichment therapy is performed for some amount of predetermined minutes (e.g., 45 or 60 minutes). The therapy can either continue or pause while a subsequent angiogram is performed and the IMR value is determined, as previously indicated.

In certain implementations, a controller (e.g., controller 102 of FIG. 1A or controller of FIG. 6) may be coupled to one or more sensors and/or receive signals generated by one or more sensors. The sensor may include flow and/or pressure sensors as described herein. In some implementations, titrating or controlling the amount of the gas-enriched blood or gas-enriched liquid delivered to the patient may be based on the detected blood flow and/or blood pressure in the vasculature or microvasculature of the patient.

In certain implementation, in a system for controlling gas-enriched therapy, one or more controllers comprising a processor, a memory, and associated circuitry communicatively coupled to the at least one sensor may receive one or more signals corresponding to a measured value of the one or more physiological parameters from one or more sensors (e.g., flow or pressure sensors). Based on the measured values, an alert or control signal for controlling an amount of the gas-enriched blood or gas-enriched liquid delivered to the patient may be generated, and control or titration of the therapy may be achieved. In certain implementation, based on the measured values, a value representing microvascular dysfunction in the vasculature of the patient may be estimated, and based on the estimated microvascular dysfunction in the vasculature of the patient, an alert or control signal for controlling an amount of the gas-enriched blood or gas-enriched liquid delivered to the patient may be generated. As a result, control or titration of the therapy may be achieved. In certain implementations, the estimated microvascular dysfunction may include a value representing microvascular obstruction or microvascular resistance.

Some implementations of subject matter and operations described in this specification (e.g., processes 500, 800) can be implemented in digital electronic circuitry, or in computer software, firmware, or hardware, including the structures disclosed in this specification and their structural equivalents, or in combinations of one or more of them. For example, in some implementations, the processor of the delivery system (e.g., delivery system 100) can be implemented using digital electronic circuitry, or in computer software, firmware, or hardware, or in combinations of one or more of them.

In an aspect, a system for controlling gas-enrichment therapy in a patient (such as system 100 described previously) can include the following. The system includes a gas-enrichment system configured to enrich a liquid with gas to form a gas-enriched liquid and to mix the gas-enriched liquid with blood to form gas-enriched blood. The system includes a plurality of fluid conduits fluidly coupled to the gas-enrichment system, a first conduit of the plurality of fluid conduits configured for flow of the blood from the patient to the gas-enrichment system, and a second conduit of the plurality of conduits configured for flow of the gas-enriched blood from the gas-enrichment system to the patient. The system includes a pump coupled to at least one conduit of the plurality of fluid conduits. The pump is configured to pump blood to and from the gas-enrichment system and the patient. The system includes at least one sensor configured to measure one or more physiological parameters indicative of a microvascular dysfunction in a vasculature of the patient. The system includes one or more controllers comprising a processor, a memory, and associated circuitry, wherein the processor is configured to perform operations. The operations include receiving one or more signals corresponding to a measured value of the one or more physiological parameters from the at least one sensor. The operations include estimating, based on the measured value, a microvascular dysfunction in the vasculature of the patient. The operations include generating, based on the estimated microvascular dysfunction in the vasculature of the patient, an alert or control signal for controlling an amount of the gas-enriched blood delivered to the patient.

In some implementations, the one or more signals correspond to a measured value of blood pressure from at least one pressure sensor, a microvascular dysfunction in the vasculature of the patient is estimated based on the measured pressure value and an alert or control signal is generated based on the estimated microvascular dysfunction. In some implementations, the one or more signals correspond to a measured value of blood flow from at least one flow sensor, a microvascular dysfunction in the vasculature of the patient is estimated based on the measured flow value and an alert or control signal is generated based on the estimated microvascular dysfunction. In some implementations, the microvascular dysfunction is microvascular obstruction. In some implementations, the microvascular dysfunction is microvascular resistance.

In an aspect, a system for controlling gas-enrichment therapy in a patient (such as system 100 described previously) can include the following. The system for controlling gas-enrichment therapy in a patient includes a gas-enrichment system configured to enrich a liquid with gas to form a gas-enriched liquid and to deliver the gas-enriched liquid into a vasculature of the patient to form gas-enriched blood. The system includes at least one conduit fluidly coupled to the gas-enrichment system, the at least one conduit configured for flow of the gas-enriched liquid from the gas-enrichment system to the patient. The system includes a pump coupled to the at least one conduit, the pump configured to pump gas-enriched liquid from the gas-enrichment system to the patient. The system includes at least one sensor configured to measure one or more physiological parameters indicative of a microvascular dysfunction in a vasculature of the patient. The system includes one or more controllers comprising a processor, a memory, and associated circuitry, wherein the processor is configured to perform operations. The operations include receiving one or more signals corresponding to a measured value of the one or more physiological parameters from the at least one sensor. The operations include estimating, based on the measured value, the microvascular dysfunction in the vasculature of the patient. The operations include generating, based on the microvascular dysfunction in the vasculature of the patient, an alert or control signal for titrating or controlling the gas-enriched liquid delivered to the patient.

In some implementations, the one or more signals correspond to a measured value of blood pressure from at least one pressure sensor, a microvascular dysfunction in the vasculature of the patient is estimated based on the measured pressure value and an alert or control signal is generated based on the estimated microvascular dysfunction.

In some implementations, the one or more signals correspond to a measured value of blood flow from at least one flow sensor, a microvascular dysfunction in the vasculature of the patient is estimated based on the measured flow value and an alert or control signal is generated based on the estimated microvascular dysfunction.

In some implementations, the microvascular dysfunction includes a microvascular obstruction.

In some implementations, the microvascular dysfunction includes a microvascular resistance.

In some implementations, a system for controlling gas-enrichment therapy in a patient includes a gas-enrichment system configured to enrich a liquid with gas to form a gas-enriched liquid and to mix the gas-enriched liquid with blood to form gas-enriched blood. A plurality of fluid conduits are fluidly coupled to the gas-enrichment system, a first conduit of the plurality of fluid conduits is configured for flow of the blood from the patient to the gas-enrichment system, and a second conduit of the plurality of conduits is configured for flow of the gas-enriched blood from the gas-enrichment system to the patient. A pump is coupled to at least one conduit of the plurality of fluid conduits, the pump is configured to pump blood to and from the gas-enrichment system and the patient and at least one sensor is configured to measure a blood flow or blood pressure for a vasculature of the patient. One or more controllers comprising a processor, a memory, and associated circuitry is included where the processor is configured for receiving one or more signals corresponding to a measured value of the blood flow from the at least one sensor; generating, based on the measured value of the blood flow or blood pressure, an alert or control signal for controlling an amount of the gas-enriched blood delivered to the patient.

In some implementations, a system for controlling gas-enrichment therapy in a patient includes a gas-enrichment system configured to enrich a liquid with gas to form a gas-enriched liquid and to deliver the gas-enriched liquid into a vasculature of the patient to form gas-enriched blood. At least one conduit is fluidly coupled to the gas-enrichment system, the at least one conduit is configured for flow of the gas-enriched liquid from the gas-enrichment system to the patient. A pump is coupled to the at least one conduit, the pump is configured to pump gas-enriched liquid from the gas-enrichment system to the patient, and at least one sensor is configured to measure a blood flow or blood pressure in a vasculature of the patient. One or more controllers comprising a processor, a memory, and associated circuitry is included where the processor is configured for receiving one or more signals corresponding to a measured value of the blood flow or blood pressure from the at least one sensor; generating, based on the blood flow or blood pressure measurement, an alert or control signal for titrating or controlling the gas-enriched liquid delivered to the patient.

Some implementations described in this specification (e.g., the processor of the delivery system, etc.) can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing, and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random-access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 9:
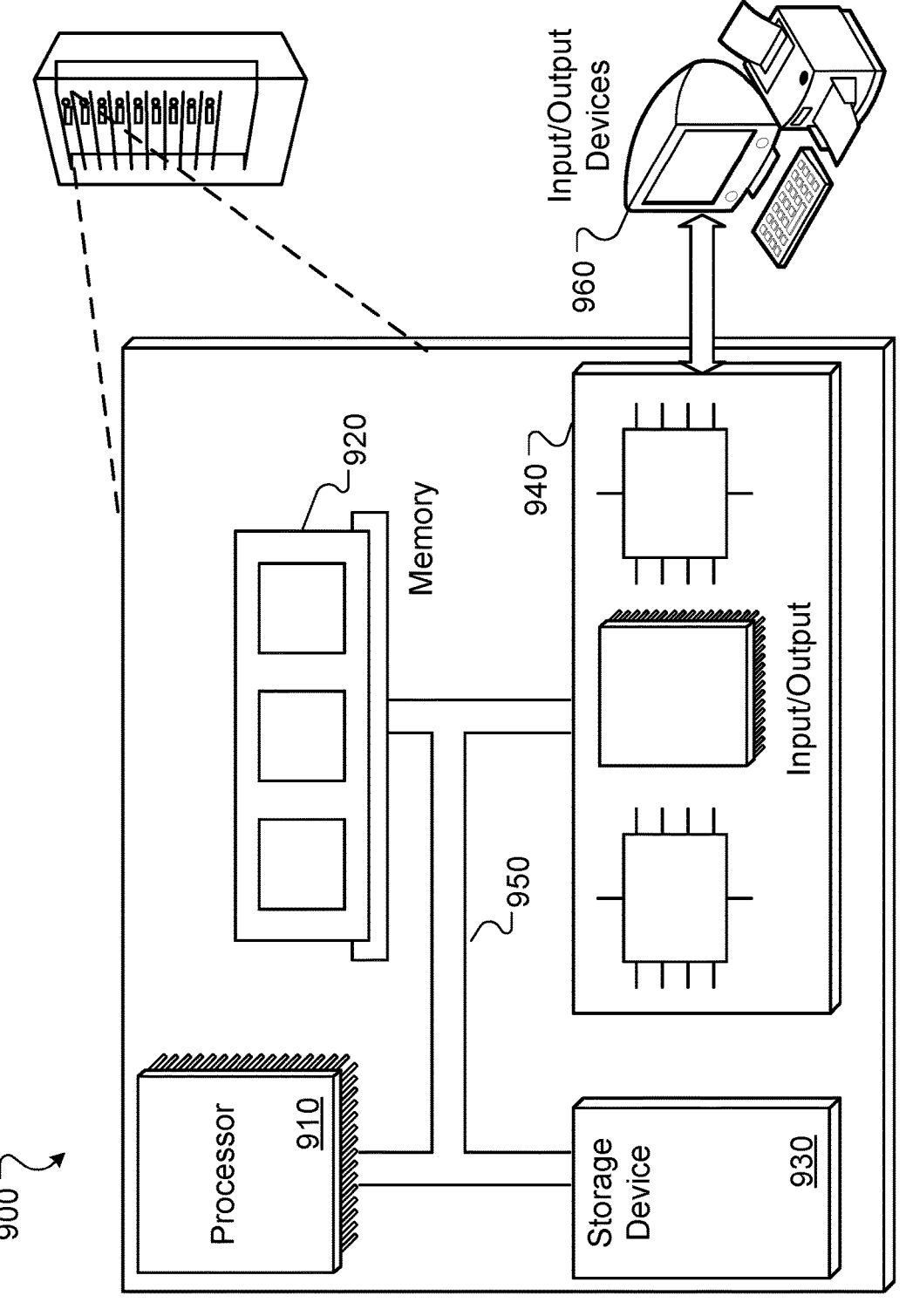
FIG. 9 shows an example computer system.

FIG. 9 shows an example computer system 900 that includes a processor 900, a memory 920, a storage device 930 and an input/output device 940. Each of the components 900, 920, 930 and 940 can be interconnected, for example, by a system bus 950. The processor 900 is capable of processing instructions for execution within the system 900. In some implementations, the processor 900 is a single-threaded processor, a multi-threaded processor, or another type of processor. The processor 900 is capable of processing instructions stored in the memory 920 or on the storage device 930. The memory 920 and the storage device 930 can store information within the system 900.

The input/output device 940 provides input/output operations for the system 900. In some implementations, the input/output device 940 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc.

In some implementations, the input/output device can include driver devices configured to receive input data and send output data to other input/output devices, e.g., keyboard, printer and display devices 960. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. For example, the detailed description and the accompanying drawings to which it refers are intended to describe some, but not necessarily all, examples or embodiments of the system. The described embodiments are to be considered in all respects only as illustrative and not restrictive. Nevertheless, various modifications may be made without departing from the scope of the data processing system described herein. Accordingly, other embodiments are within the scope of the following claims.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

As used herein, including in the claims, "and" as used in a list of items prefaced by "at least one of" indicates a disjunctive list such that, for example, a list of "at least one of A, B, and C" means A or B or C or AB or AC or BC or ABC (i.e., A and B and C), or combinations with more than one feature (e.g., AA, AAB, ABBC, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify the application of the invention. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one invention may be disclosed.

Other embodiments are within the scope of the invention. For example, due to the nature of software, functions described above can be implemented using software, hardware, firmware, hardwiring, or combinations of any of these. Features implementing functions may also be physically located at various locations, including being distributed such that portions of functions are implemented at different physical locations.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A system for controlling gas-enrichment therapy in a patient, the system comprising:

a gas-enrichment system configured to enrich a liquid with gas to form a gas-enriched liquid and to mix the gas-enriched liquid with blood to form gas-enriched blood;

a plurality of conduits fluidly coupled to the gas-enrichment system, a first conduit of the plurality of conduits configured for flow of the blood from the patient to the gas-enrichment system, and a second conduit of the plurality of conduits configured for flow of the gas-enriched blood from the gas-enrichment system to the patient;

a pump coupled to at least one conduit of the plurality of conduits, the pump configured to pump blood to and from the gas-enrichment system and the patient;

a wire configured to extend into a vasculature of the patient and comprising at least one pressure sensor configured to measure a blood pressure in the vasculature of the patient, the blood pressure indicative of a microvascular resistance in the vasculature of the patient; and a controller comprising a processor, a memory, and associated circuitry communicatively coupled to the pressure sensor, wherein the processor is configured to perform operations comprising:

receiving one or more signals corresponding to a measured blood pressure from the at least one pressure sensor;

estimating, based on the measured blood pressure, a microvascular resistance in the vasculature of the patient; and generating, based on the estimated microvascular resistance in the vasculature of the patient, an alert or control signal for controlling an amount of the gas-enriched blood delivered to the patient.

2. The system of claim 1, the operations further comprising:

determining a change in the microvascular resistance of the vasculature of the patient; and generating based on the determined change in microvascular resistance, the alert or control signal for controlling an amount of the gas-enriched blood delivered to the patient.

3. The system of claim 1, further comprising a flow sensor that measures a flow rate of blood in the vasculature of the patient, wherein estimating the microvascular resistance in the vasculature of the patient is based on the flow rate.

4. The system of claim 1, the operations further comprising:

sending the control signal to the pump during operation of the pump for delivery of the gas-enriched blood to the patient; and causing, based on sending the control signal, the pump to increase a pump speed or reduce a pump speed to increase or reduce the amount of the gas-enriched blood delivered to the patient.

5. The system of claim 1, wherein controlling the amount of the gas-enriched blood delivered to the patient comprises:

determining that a change in the measured value of the blood pressure represents a reduced microvascular resistance in the vasculature of the patient; and in response to determining that the change in the measured value represents the reduced microvascular resistance, generating the control signal that is configured to cause a reduction in the amount of the gas-enriched blood delivered to the patient.

6. The system of claim 1, wherein controlling the amount of the gas-enriched blood delivered to the patient comprises:

determining that a change in the measured value of the blood pressure represents an increased microvascular resistance in the vasculature of the patient; and in response to determining that the change in the measured value represents the increased microvascular resistance, generating the control signal that is configured to cause an increase in the amount of the gas-enriched blood delivered to the patient.

7. The system of claim 1, further comprising a flow sensor that measures a flow rate of the blood in the vasculature of the patient, and wherein the operations further comprise:

estimating a change in the microvascular resistance in the patient based on a ratio of the blood pressure and the flow rate; and generating the control signal based on the estimated microvascular resistance.

8. The system of claim 1, wherein generating the control signal is performed in real-time or near-real time during delivery of the gas-enriched blood to the patient, wherein the delivery of the gas-enriched blood to the patient is not paused during measurement of the blood pressure, and wherein the measurement of the blood pressure represents a status of the patient for the delivery of the gas-enriched blood to the patient.

9. The system of claim 8, wherein real-time or near-real time comprises processing, by the controller, data received from the pressure sensor as soon as the data are available to the controller and generating the control signal based on the processing.

10. The system of claim 1, wherein receiving one or more signals corresponding to the measured value of the blood pressure from the pressure sensor comprises receiving a series of measured values of the blood from the pressure sensor, the series of measured values corresponding to a period of time during delivery of the gas-enriched blood to the patient, and wherein the operations further comprise:

determining, based on the series of measured values corresponding to the period of time, whether a value of the blood pressure is increasing or decreasing over time; and generating, based on determining that the value of the one or more physiological blood pressure is increasing or decreasing over time, the control signal that is configured to increase or reduce the amount of the gas-enriched blood delivered to the patient.

11. The system of claim 1, wherein the operations further comprise:

receiving angiogram data from an imaging device in communication with the controller, the angiogram data representing the patient for a time period contemporaneous with delivery of the gas-enriched blood to the patient;

determining an index of microcirculatory resistance (IMR) value from the angiogram data; and generating, based on the angiogram data and determined IMR value or change in IMR value, the control signal configured to increase or reduce the amount of the gas-enriched blood delivered to the patient.

12. A system for controlling gas-enrichment therapy in a patient, the system comprising:

a gas-enrichment system configured to enrich a liquid with gas to form a gas-enriched liquid and to deliver the gas-enriched liquid into a vasculature of the patient to form gas-enriched blood;

at least one conduit fluidly coupled to the gas-enrichment system, the at least one conduit configured for flow of the gas-enriched liquid from the gas-enrichment system to the patient;

a pump coupled to the at least one conduit, the pump configured to pump gas-enriched liquid from the gas-enrichment system to the patient;

a wire configured to extend into a vasculature of the patient and comprising at least one pressure sensor configured to measure a blood pressure in the vasculature of the patient, the blood pressure indicative of a microvascular resistance in the vasculature of the patient; and a controller comprising a processor, a memory, and associated circuitry communicatively coupled to the pressure sensor, wherein the processor is configured to perform operations comprising:

receiving one or more signals corresponding to a measured blood pressure from the at least one pressure sensor;

estimating, based on the measured blood pressure, the microvascular resistance in the vasculature of the patient; and generating, based on the microvascular resistance in the vasculature of the patient, an alert or control signal for titrating or controlling an amount of the gas-enriched liquid delivered to the patient.

13. The system of claim 12, the operations further comprising:

determining a change in the microvascular resistance of the vasculature of the patient; and generating based on the determined change in microvascular resistance, the alert or control signal for titrating or controlling the gas-enriched liquid delivered to the patient.

14. The system of claim 12, further comprising a flow sensor that measures a flow rate of blood in the vasculature of the patient, wherein estimating the microvascular resistance in the vasculature of the patient is based on the flow rate.

15. The system of claim 12, the operations further comprising:

sending the control signal to the pump during operation of the pump for delivery of the gas-enriched liquid to the patient; and causing, based on sending the control signal, the pump to increase a pump speed or reduce a pump speed to increase or reduce an amount of the gas-enriched liquid delivered to the patient.

16. The system of claim 12, wherein controlling the gas-enriched blood delivered to the patient comprises:

determining that a change in the measured value of the blood pressure represents a reduced microvascular resistance in the vasculature of the patient; and in response to determining that the change in the measured value represents the reduced microvascular resistance, generating the control signal that is configured to cause a reduction in the amount of the gas-enriched blood delivered to the patient.

17. The system of claim 12, wherein controlling the gas-enriched liquid delivered to the patient comprises:

determining that a change in the measured value of the blood pressure represents an increased microvascular resistance in the vasculature of the patient; and in response to determining that the change in the measured value represents the increased microvascular resistance, generating the control signal that is configured to cause an increase in the amount of the gas-enriched blood delivered to the patient.

18. The system of claim 12, further comprising a flow sensor that measures a flow rate of the blood in the vasculature of the patient, and wherein the operations further comprise:

estimating a change in microvascular resistance in the patient based on a ratio of the blood pressure and the flow rate; and generating the control signal based on the estimated microvascular resistance.

19. The system of claim 12, wherein generating the control signal or alert is performed in real-time or near-real time during delivery of the gas-enriched liquid to the patient, wherein the delivery of the gas-enriched liquid to the patient is not paused during measurement of the blood pressure, and wherein the measurement of the blood pressure represents a contemporaneous status of the patient for the delivery of the gas-enriched liquid to the patient.

20. The system of claim 19, wherein real-time or near-real time comprises processing, by the controller, data received from the pressure sensor as soon as the data are available to the controller and generating the control signal or alert based on the processing.

21. The system of claim 12, wherein receiving one or more signals corresponding to the measured value of the blood pressure from the pressure sensor comprises receiving a series of measured values of the blood from the pressure sensor, the series of measured values corresponding to a period of time during delivery of the gas-enriched blood to the patient, and wherein the operations further comprise:

determining, based on the series of measured values corresponding to the period of time, whether a value of the blood pressure is increasing or decreasing over time; and generating, based on determining that the value of the blood pressure is increasing or decreasing over time, the control signal that is configured to increase or reduce the amount of the gas-enriched blood delivered to the patient.

22. The system of claim 12, wherein the operations further comprise:

receiving angiogram data from an imaging device in communication with the controller, the angiogram data representing the patient for a time period contemporaneous with delivery of the gas-enriched blood to the patient;

determining an index of microcirculatory resistance (IMR) value from the angiogram data; and generating, based on the angiogram data and determined IMR value or change in IMR value, the control signal configured to increase or reduce the amount of the gas-enriched blood delivered to the patient.

\* \* \* \* \*